United States Patent [19]

Ensminger et al.

[11] Patent Number: 5,527,278
[45] Date of Patent: Jun. 18, 1996

[54] IMPLANTABLE ACCESS DEVICES

[75] Inventors: William D. Ensminger; Robert F. Gavin, both of Ann Arbor, Mich.

[73] Assignee: Michigan TransTech Corporation, Ann Arbor, Mich.

[21] Appl. No.: 467,268

[22] Filed: Jun. 6, 1995

Related U.S. Application Data

[63] Continuation of Ser. No. 407,483, Mar. 15, 1995, Pat. No. 5,476,451, which is a continuation of Ser. No. 259,053, Jun. 13, 1994, Pat. No. 5,417,656, which is a continuation of Ser. No. 148,394, Nov. 8, 1993, Pat. No. 5,350,360, which is a division of Ser. No. 940,619, Sep. 4, 1992, Pat. No. 5,281,199, which is a continuation-in-part of Ser. No. 818,626, Jan. 10, 1992, Pat. No. 5,226,879, which is a continuation-in-part of Ser. No. 654,661, Feb. 15, 1991, Pat. No. 5,180,365, which is a continuation-in-part of Ser. No. 539,793, Jul. 18, 1990, Pat. No. 5,053,013, which is a continuation-in-part of Ser. No. 487,541, Mar. 1, 1990, Pat. No. 5,057,084.

[51] Int. Cl.$^6$ ............................................. A61M 11/00
[52] U.S. Cl. ........................... 604/93; 604/49; 604/175
[58] Field of Search ............................ 604/93, 49, 174, 604/175, 245–249, 280, 283, 905

[56] References Cited

U.S. PATENT DOCUMENTS

| | | |
|---|---|---|
| 3,288,137 | 1/1964 | Lund . |
| 3,402,710 | 9/1968 | Paleschuck . |
| 3,565,078 | 2/1971 | Vaillancourt et al. . |
| 3,699,956 | 10/1972 | Kitrilakis . |
| 4,181,132 | 1/1980 | Parks . |
| 4,190,040 | 2/1980 | Schulte . |
| 4,230,109 | 10/1980 | Geiss . |
| 4,256,102 | 3/1981 | Monaco . |
| 4,314,568 | 2/1982 | Loving . |
| 4,387,879 | 6/1983 | Tauschinski . |
| 4,405,320 | 9/1983 | Cracauer et al. . |
| 4,425,119 | 1/1984 | Berglund . |
| 4,430,081 | 2/1984 | Timmermans . |
| 4,439,188 | 3/1984 | Dennehey et al. . |
| 4,447,237 | 5/1984 | Frisch et al. . |
| 4,464,178 | 10/1984 | Dalton . |
| 4,490,137 | 12/1984 | Moukheibir . |
| 4,491,126 | 1/1985 | Cullor . |
| 4,534,759 | 8/1985 | Trawöger . |
| 4,543,088 | 9/1985 | Bootman et al. . |
| 4,547,194 | 10/1985 | Moorehead . |
| 4,569,675 | 2/1986 | Prosl et al. . |
| 4,578,061 | 3/1986 | Lemelson . |
| 4,578,063 | 3/1986 | Inmann et al. . |
| 4,581,020 | 4/1986 | Mittlemab . |
| 4,623,329 | 11/1987 | Drobish et al. . |
| 4,634,422 | 1/1987 | Kantrowitz et al. . |
| 4,645,495 | 2/1987 | Vaillancourt . |
| 4,650,473 | 3/1987 | Bartholomew et al. . |
| 4,673,394 | 6/1987 | Fenton, Jr. et al. . |
| 4,682,981 | 7/1987 | Suzuki et al. . |
| 4,692,146 | 9/1987 | Hilger . |
| 4,695,273 | 9/1987 | Brown . |

(List continued on next page.)

FOREIGN PATENT DOCUMENTS

| | | |
|---|---|---|
| 0119596 | 3/1984 | European Pat. Off. . |
| 134745 | 8/1984 | European Pat. Off. . |
| 0132940A1 | 7/1985 | European Pat. Off. . |
| 1296652 | 5/1962 | France . |
| 3242870 | 6/1983 | Germany . |
| 3528878 | 2/1987 | Germany . |
| 2192338 | 1/1988 | United Kingdom . |
| 8300367 | 2/1983 | WIPO . |

*Primary Examiner*—John D. Yasko
*Attorney, Agent, or Firm*—Harness, Dickey & Pierce

[57] ABSTRACT

An access port for implantation within the body of a patient for providing repeated access to a specific site within the patient and communicating with the site by an implanted internal catheter. The access ports in accordance with this invention include a housing having an inlet orifice leading to a reduced diameter guide passageway. An external filament such as a needle, guide wire, optical fiber, or external catheter can be introduced into the access device and fed through the housing. The system allows the introduction of therapeutic agents, the removal of fluids from the body, or the introduction of sensing or articulating devices to the specific site within the patient.

9 Claims, 14 Drawing Sheets

U.S. PATENT DOCUMENTS

| | | |
|---|---|---|
| 4,704,103 | 11/1987 | Stober et al. . |
| 4,710,167 | 12/1987 | Lazorthes . |
| 4,710,174 | 12/1987 | Moden et al. . |
| 4,712,583 | 12/1987 | Pelmulder et al. . |
| 4,781,680 | 11/1988 | Redmond et al. . |
| 4,781,693 | 11/1988 | Martinez et al. . |
| 4,781,695 | 11/1988 | Dalton . |
| 4,790,826 | 12/1988 | Elftman . |
| 4,810,241 | 3/1989 | Rogers . |
| 4,832,054 | 5/1989 | Bark . |
| 4,842,591 | 6/1989 | Luther . |
| 4,857,053 | 8/1989 | Dalton . |
| 4,857,062 | 8/1989 | Russell . |
| 4,886,501 | 12/1989 | Johnston et al. . |
| 4,915,690 | 4/1990 | Cone et al. . |
| 4,929,235 | 5/1990 | Merry et al. . |
| 4,978,338 | 12/1990 | Melsky . |
| 5,026,344 | 6/1991 | Dijkstra et al. . |
| 5,041,098 | 8/1991 | Loiterman et al. . |
| 5,045,060 | 9/1991 | Melsky et al. . |
| 5,053,013 | 10/1991 | Ensminger et al. . |
| 5,057,084 | 10/1991 | Ensminger et al. . |
| 5,092,849 | 3/1992 | Sampson . |
| 5,171,228 | 12/1992 | McDonald . |
| 5,180,365 | 1/1993 | Ensminger et al. . |
| 5,226,879 | 7/1993 | Ensminger et al. . |
| 5,263,930 | 11/1993 | Ensminger et al. . |
| 5,281,199 | 1/1994 | Ensminger et al. . |
| 5,318,545 | 6/1994 | Tucker . |
| 5,350,360 | 9/1994 | Ensminger et al. . |
| 5,352,204 | 10/1994 | Ensminger . |
| 5,356,381 | 10/1994 | Ensminger et al. . |
| 5,395,324 | 3/1995 | Hinrichs . |
| 5,417,656 | 5/1995 | Ensminger et al. . |

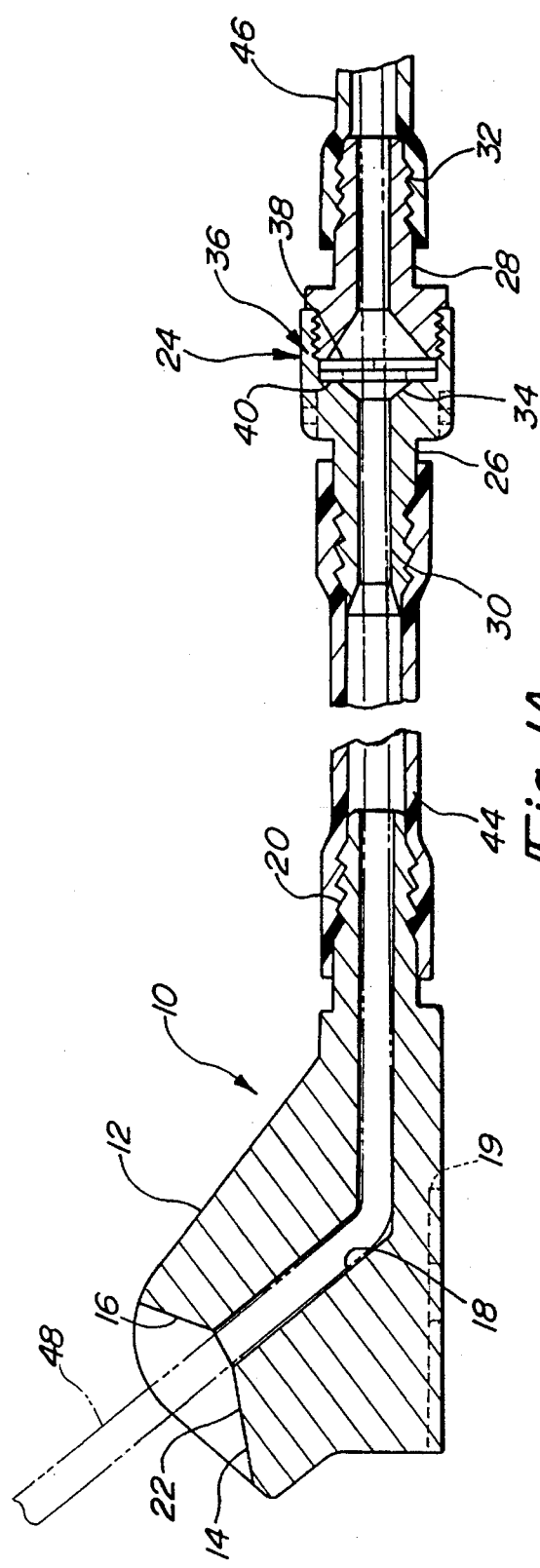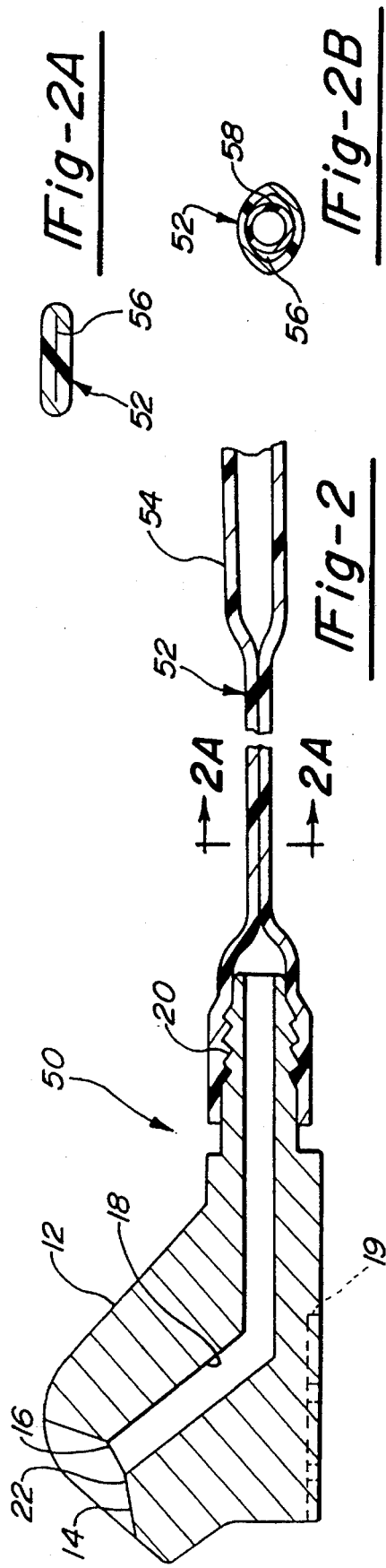

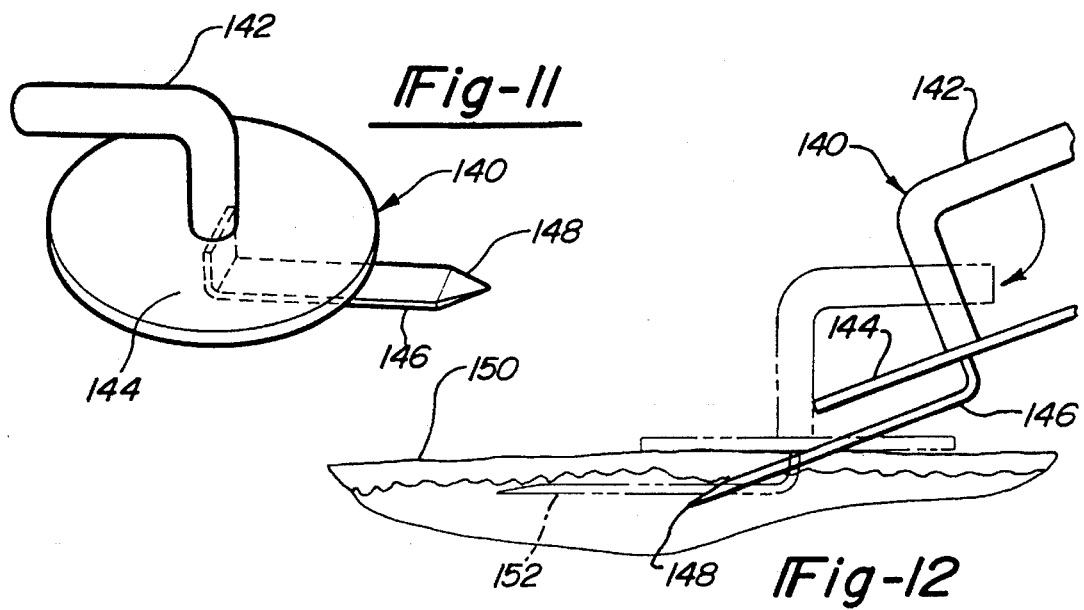
Fig-11
Fig-12
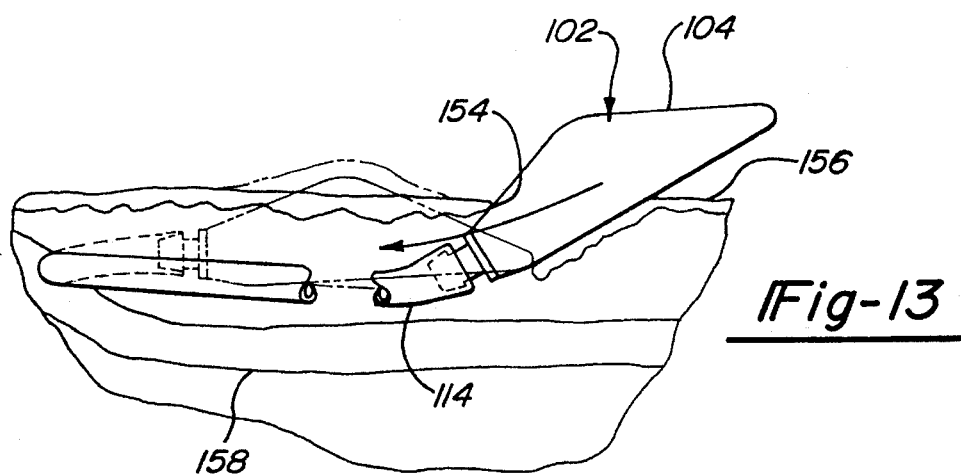
Fig-13
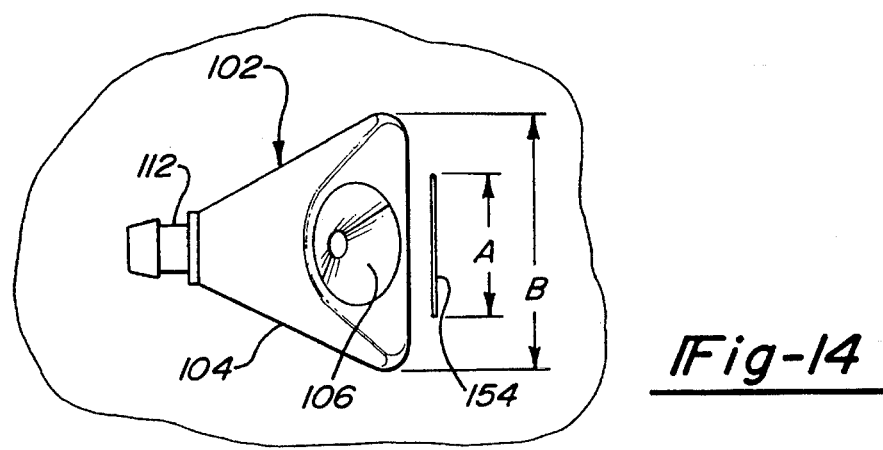
Fig-14

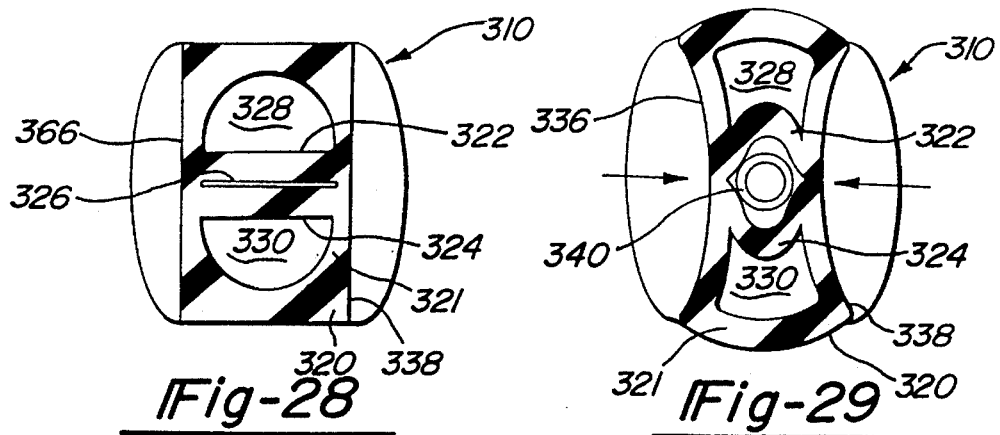
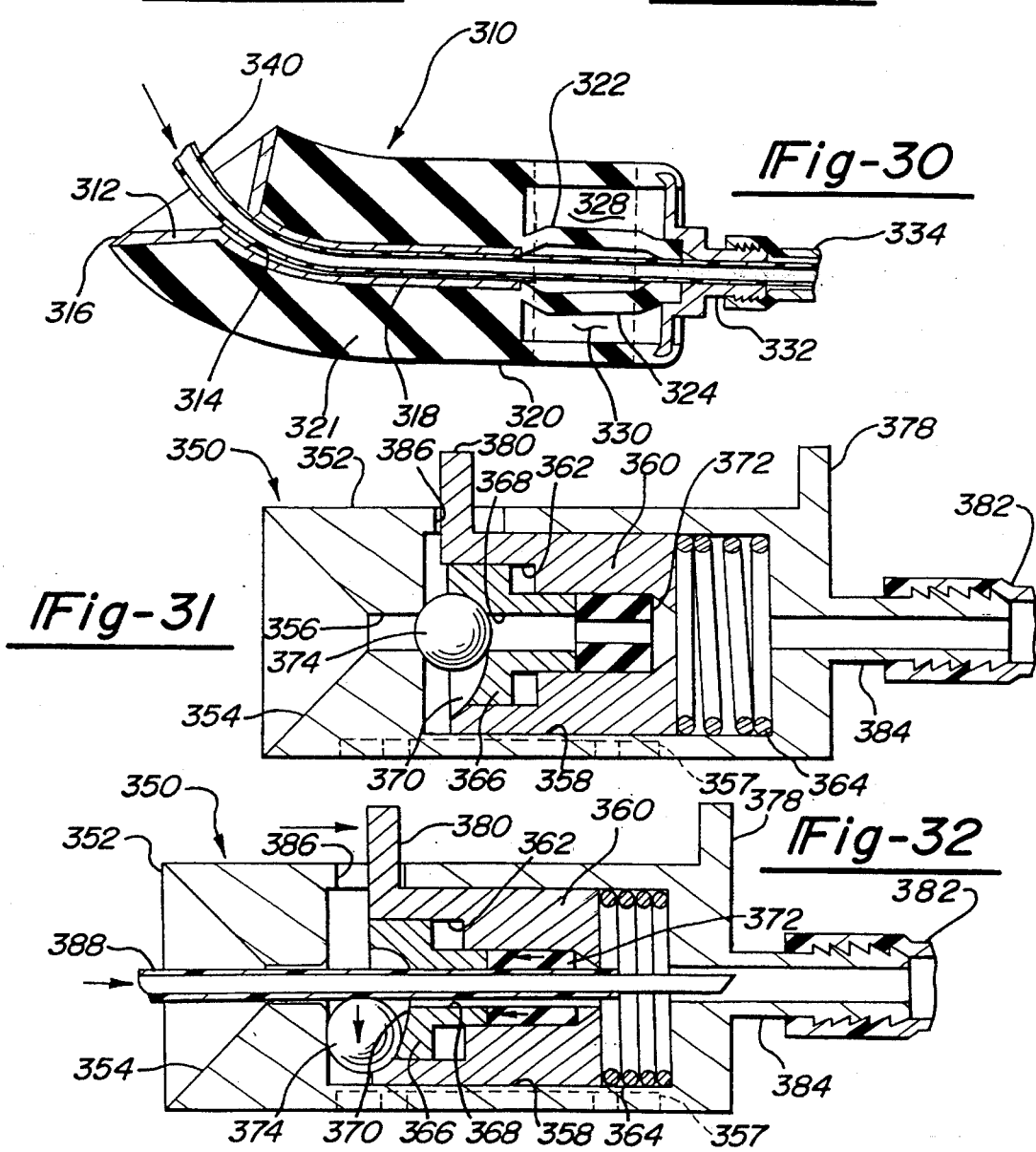

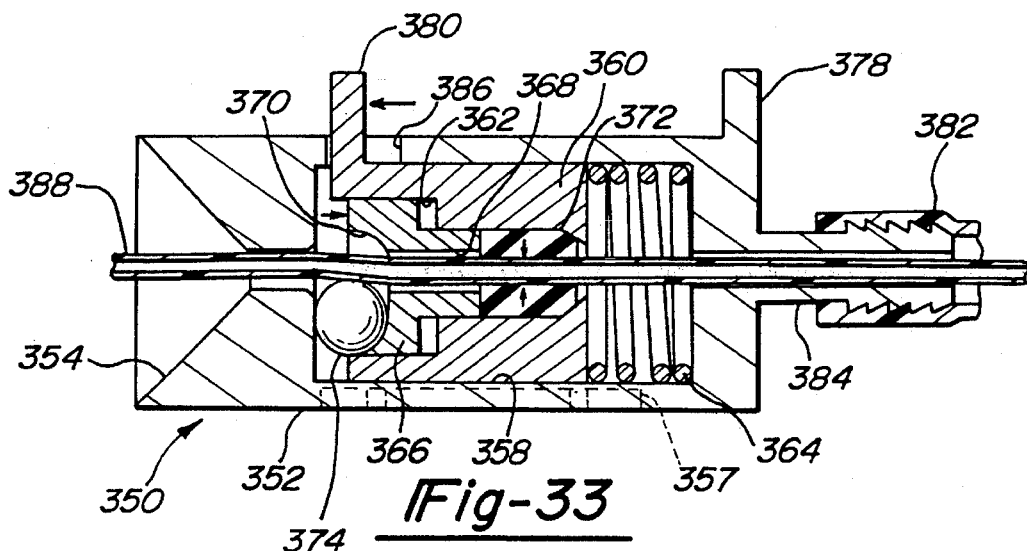
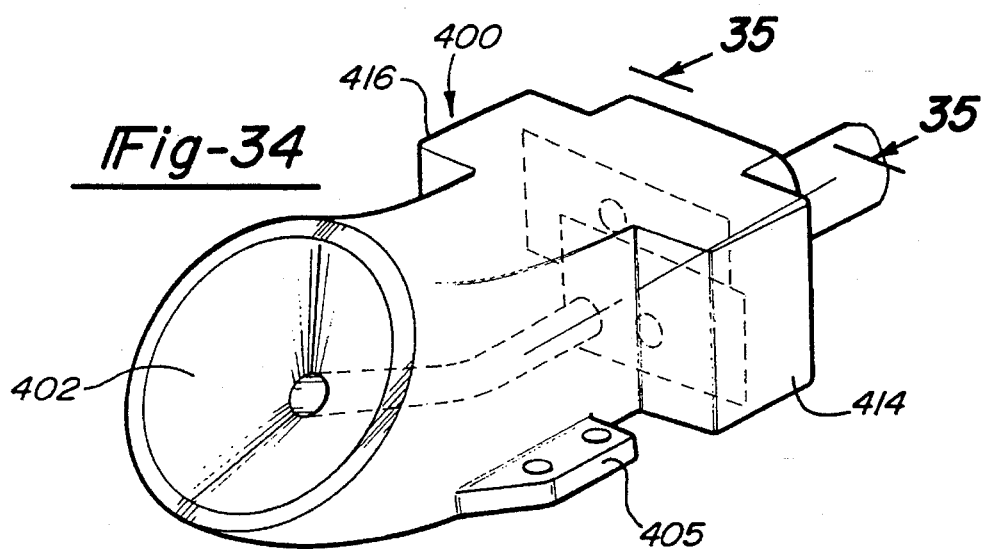
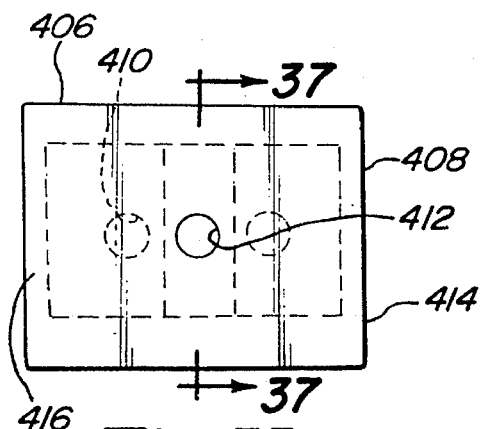
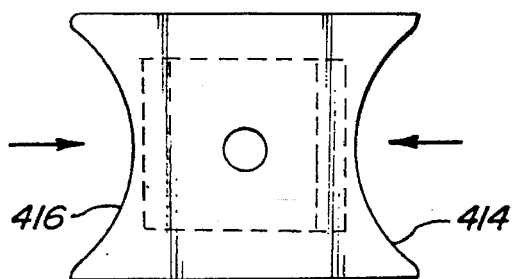

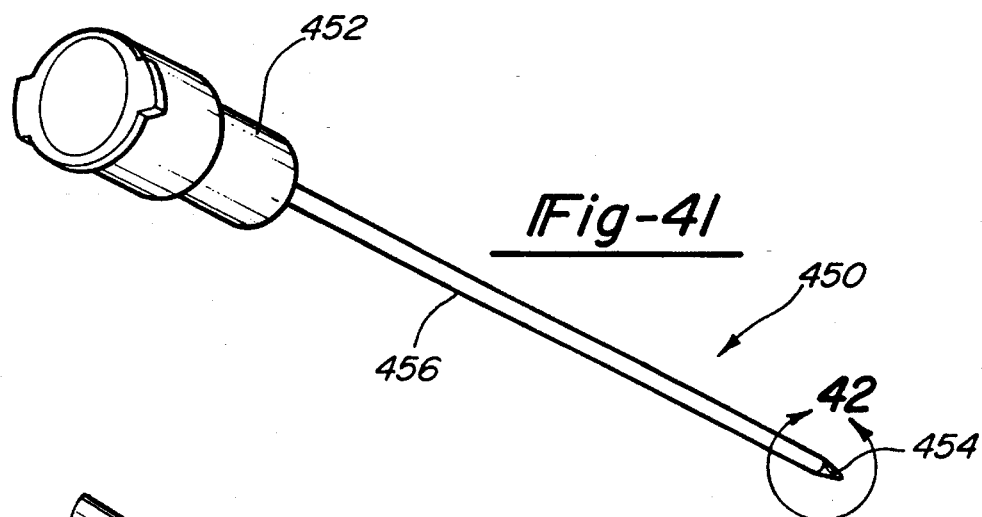
*Fig-41*
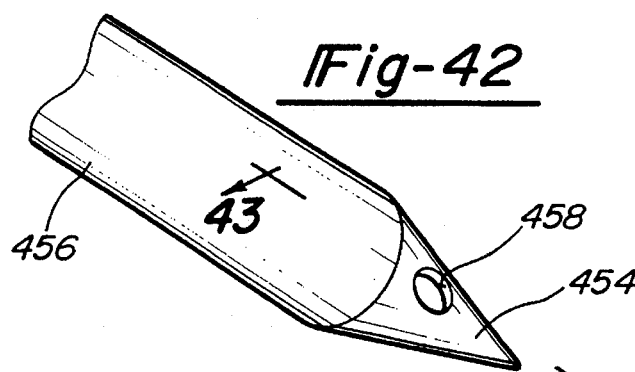
*Fig-42*
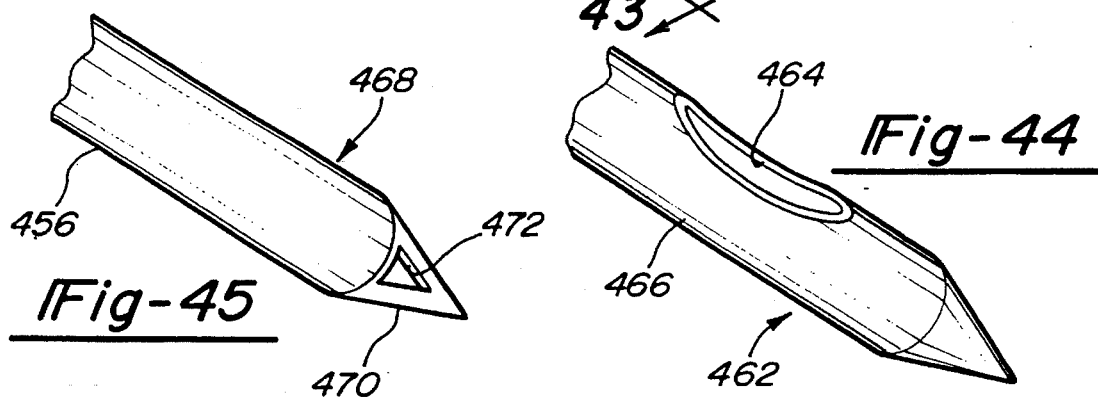
*Fig-44*
*Fig-45*
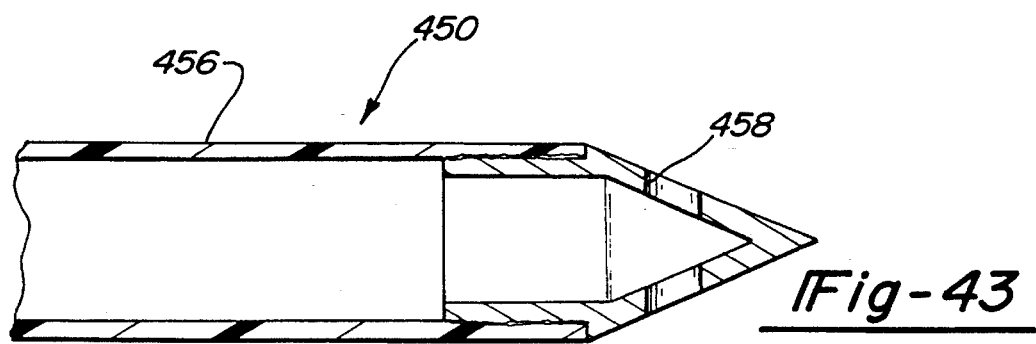
*Fig-43*

IMPLANTABLE ACCESS DEVICES

CROSS-REFERENCE TO RELATED APPLICATIONS

This application is a continuation of U.S. patent application Ser. No. 08/407,483, filed Mar. 15, 1995, now U.S. Pat. No. 5,476,451 which is a continuation of U.S. patent application Ser. No. 08/259,053, filed Jun. 13, 1994, now U.S. Pat. No. 5,417,656 which is a continuation of U.S. patent application Ser. No. 08/148,394, filed Nov. 8, 1993 now issued U.S. Pat. No. 5,350,360, which is a divisional of U.S. patent application Ser. No. 07/940,619, filed Sep.4, 1992 now issued U.S. Pat. No. 5,281,199 which is a continuation-in-part of U.S. application Ser. No. 818,626 filed on Jan. 10, 1992 now U.S. Pat. No. 5,226,879, entitled "Implantable Infusion Device" which is a continuation-in-part of U.S. application Ser. No. 654,661, filed on Feb. 15, 1991 now U.S. Pat. No. 5,180,365, which is a continuation-in-part of U.S. application Ser. No. 539,793 filed on Jul. 18, 1990 now issued as U.S. Pat. No. 5,053,013, which is a continuation-in-part of U.S. application Ser. No. 487,541 filed on Mar. 1, 1990 now issued as U.S. Pat. No. 5,057,084; the disclosures of which are hereby incorporated by reference and are collectively referred to as "related applications" herein.

FIELD OF THE INVENTION

This invention relates to a device for introducing a filament, such as a catheter, into a patient for infusing a therapeutic agent to a desired site or withdrawing a fluid from a desired site within a patient. More particularly, the invention relates to devices which are implanted such that no portion is transcutaneous. Its access portion is subcutaneous but designed so as to facilitate repeated access by the percutaneous route.

BACKGROUND AND SUMMARY OF THE INVENTION

In current human and animal medical practice, there are numerous instances where therapeutic agents must be delivered to a specific organ or a tissue within the body. An example is the infusion of chemotherapy into a central vein on a recurring basis over a lengthy treatment period for widespread sites of malignant tumor. Without an infusion device for intravenous drug infusion, multiple vein punctures over a lengthy period would result in progressive thrombosis, venous sclerosis, and destruction of small diameter peripheral vessels. In other cases, it may be desirable to infuse chemotherapy to a localized malignant tumor site. It may be difficult or impossible to deliver an agent specifically to such a site on a regular repetitive basis without surgically implanting an infusion system. Similarly, repeated arterial access is occasionally needed for injection of an X-ray dye or contrast agent into an artery for diagnostic purposes. In other situations, there is a need to repetitively remove a body fluid for analysis from a remote body site. Finally, sensing and physiological measuring devices Incorporated into small diameter catheters and optical fibers are increasingly being utilized for monitoring body processes and could be more easily implemented through a properly designed access device with an adequate internal diameter.

In prior medical practice, percutaneous catheters have been used to provide vascular or organ access for drug therapy or the withdrawal of body fluids. Although such systems generally performed in a satisfactory manner, numerous problems were presented by such therapy approaches, including the substantial care requirements of the patients, e.g. dressing changes with sterile techniques, a significant rate of infection of the catheter because of its transcutaneous position, and a high rate of venous thrombosis, particularly if the catheter was located within an extremity vein.

Implantable infusion devices or "ports" have recently become available and represent a significant advance over transcutaneous catheters. Presently available infusion ports have a number of common fundamental design features. The ports themselves comprise a housing which forms a reservoir that can be constructed from a variety of plastic or metal materials. A surface of the reservoir is enclosed by a high-density, self-sealing septum, typically made of silicone rubber. Connected to the port housing is an implanted catheter which communicates with a vein or other site within the patient where the infusion of therapeutic agents is desired. Implantation of such devices generally proceeds by making a small subcutaneous pocket in an appropriate area of the patient under local anesthesia. The implanted catheter is tunnelled to the desired infusion site. When the physician desires to infuse or remove materials through the port, a hypodermic needle is used which pierces the skin over the infusion port and is placed into the port.

Although the presently available implantable infusion ports generally operate in a satisfactory manner, they have a number of shortcomings. Since these devices rely on a compressed rubber septum for sealing and since large diameter needles can seriously damage the septum, there are limitations in the diameter of needles which can be used to penetrate the septum. These diameter limitations severely restrict the opportunities provided by the port. In cases where it is desirable to infuse drugs using a flexible external catheter, the catheter must be fed through the needle that penetrates the septum. Such catheters have art extremely small inside diameter and, therefore, impose severe limitations on fluid flow rate and limit the types of fibers which can be introduced.

During prolonged infusions using a conventional port, the infusion needle is taped to the patient's skin to hold it in position. Conventional ports do not allow the needle to penetrate deeply into the port. Because of this, a small displacement of the needle can cause it to be pulled from the port. In cases where locally toxic materials are being infused, extravasation of such materials can cause local tissue damage which may require corrective surgery such as skin grafting or removal of tissue.

Presently available implantable drug infusion devices also have a significant size to provide an acceptable target surface area for the physician who must locate the port and penetrate the septum with a needle. The port housing becomes bulky as the septum size increases since structure is required to maintain the septum in compression to provide self-sealing after the needle is removed. Moreover, presently available infusion ports are difficult to clear if thrombosis occurs within the port or within the implanted catheter since it is difficult, if not impossible, to feed a cleaning wire through the penetrating hypodermic needle in a manner which will clear the infusion device and the internal catheter. Present infusion ports, also have a retained volume beneath the self-sealing septum which increases the volume of drug which must be administered to enable a desired quantity to reach the infusion site. This retained volume also poses problems when a physician desires to successively deliver multiple drugs to the same infusion site which are incompatible when mixed. Additionally, when it is desired to withdraw blood through the port, the retained volume of the prior art infusion ports comprises an area where blood clotting can occur, thus interfering with future access to the site. And finally, for present infusion ports, there is a risk that the physician attempting to pierce the port septum will not properly enter it, leading to the possibility of extravasation which can cause significant undesirable consequences as mentioned above.

The present Invention relates to a family of implantable infusion ports which provide numerous enhancements over prior art devices. In accordance with this invention, an infusion port is provided which incorporates the funnel-shaped entrance orifice which narrows down to a reduced diameter guide passageway. The guide passageway terminates at an internal cavity which retains an articulating catheter valve, such as a multi-element leaflet valve assembly. The port also has an exit passageway which is connected to an implanted catheter. This application describes numerous embodiments of alternative designs of patient access ports within the scope of the present invention.

In certain patient treatment applications there may be a need to provide an access port in which point of access is remote from the port valve. In prior embodiments of this invention, as described in the related applications, the patient access port has a housing which provides a valve chamber housing a valve which normally prevents the passage of fluids but which can be penetrated by an external flexible filament to permit access with the implanted catheter. In accordance with one aspect of the present invention, an access system is described in which an access housing is remote from the valve, and the components are connected by a flexible conduit. The implanted catheter is placed between the valve and the desired patient access site.

In prior embodiments of the present invention, various valving systems were described and claimed, including leaflet valves, ball valves, "flapper" type valves, etc. Each of these valve configurations is broadly encompassed by the description "articulating catheter valve" or "articulating valve", meaning that one or more valve elements are displaced in some predictable manner to provide access and which returns to an original position to provide a fluid seal. This type of valving scheme is distinguishable from those of the prior art which incorporate a compressed rubber septum which is repeatedly penetrated by a needle which leads to destruction and damage to the valving system. In accordance with one aspect of the present invention another vaiving configuration is described which is also considered an articulating valve. This alternative configuration valve is in the form of an elongated passageway formed of an elastomeric material which normally is maintained in a flattened occluded condition, but which can be penetrated by an external filament to cause it to open to provide access. Such a valve configuration can be incorporated within the housing of an access port or can be in the form of a tube attached to the outlet of an access housing.

In certain patient therapeutic applications there is a need to simultaneously infuse two incompatible materials or withdraw fluid from one site while infusing to another. One example of such application is in hemodialysis in which blood is drawn from a peripheral vein, treated, and thereafter returned to the patient. In such applications, a pair of access routes is required. In accordance with one aspect of the present invention, an access port is provided which has two separate and distinct access passageways defined by separate entrance orifices, valves and outlets, all incorporated into a single housing. This "dual port" can be connected to separate and distinct implanted catheters, or to a dual lumen catheter. In order to provide the clinician with an indication of the differences between intended functions of the two access port entrance orifices external indicating features can be formed on the access housing which can be palpated by the clinician.

As a means of facilitating the use of implanted access ports, there is a continuing need to facilitate the implantation process in a manner which minimizes trauma to the patient and simplifies the implantation procedure. In accordance with an aspect of this invention, an infusion port is provided having a housing shaped to facilitate its insertion through a narrow incision placed in the patient, for example, in the forearm area. By providing the housing with a tapered "dart" configuration, an incision having a width narrower than the cross-sectional width of the port can be used. The port housing is inserted through the narrow incision causing the skin to be slightly stretched around the incision area during port placement which causes the skin upon returning to its unstretched condition to aid in retaining the port in position. This invention also involves a special surgical tool which forms a slit in the skin and a subcutaneous pocket which is shaped to fit to accommodate an implanted access port.

Access ports in accordance with the prior disclosed embodiments of this invention have been described as being formed of a hard material such as stainless steel, titanium or other metals. Although the use of hard materials such as a metal or ceramic is needed in the entrance orifice area where a sharp instrument such as a needle or trocar would be used to access the device, resistance to damage by a sharp instrument is generally not required in other portions of the access port. As a means of increasing design flexibility and perhaps reducing cost of production of access ports, another aspect of this invention is to form a composite port, made from several materials. A hard material would be used to form the inside surface of the entrance orifice which would guide any sharp accessing instrument to the entrance orifice focus area and thereafter into an internal passageway. Another material for example, a moldable polymeric material, could be used to form the remainder of the port. The described composite port further features a smoothly bent passageway which acts as a "needle stop" which is believed to provide advantages over prior embodiments in which the passageway has an abrupt change in direction.

In previous embodiments of access ports in accordance with this invention, the access port is used to access a single site within the patient. There are however, potential applications where there may be a need to access several sites using a single access port. Accordingly, the present invention contemplates access systems in which a "bifurcated" flow path is provided. In accordance with this invention, a pair of valves are placed in series with a branching flow path between the valves. Access to one site is provided by penetrating only one valve, by penetrating both valves, the second site is accessed. Another embodiment of a bifurcated flow system involves use of a branched implanted catheter where the flow path is defined through the use of a steerable guidewire or catheter having a bent end which is directed into one of the plural branching pathways.

In embodiments of access ports previously described in the related applications, the mechanism for causing the articulating valve to open is direct engagement between an external filament and a valve element. Other types of valve actuation approaches are possible which may be advantageous in certain port applications. In accordance with this invention, several embodiments of access ports are described in which the valve mechanism is directly actuated through external palpation and thus opening of the valve does not depend solely upon direct contact between the external filament and a valve element.

In some of the previous designs of access devices in accordance with this invention which are designed to be accessed using a sharp instrument such as a needle or trocar which is used to introduce a flexible filament, there is a feature referred to as a "needle stop" in the port entrance passageway which prevents the needle from contacting and possibly damaging the valve element. In the prior embodiments such a needle stop is provided by the passageway having a change in direction which a rigid element cannot negotiate between the entrance orifice and the valve. In accordance with another aspect of the present invention, an alternate scheme for a needle stop is provided in the form of a passageway having a decreasing inside diameter. When a needle is used to access the device and the flexible external filament is fed through the inside of the needle, the needle is stopped as the passageway diameter decreases to less than the outside diameter of the needle.

Various accessing approaches are possible using the access ports in accordance with the present invention including conventional needles, sharp trocars, blunt instruments, and catheter-over-needle combinations such as the "Angiocath"™. Yet another aspect of this invention is another access instrument which combines the skin penetration capabilities of a sharpened metal object with the flexibility of an external filament. Several embodiments of composite accessing filaments are described herein in which a flexible or semi-flexible catheter is used having a sharpened hard end surface for skin penetration. These devices, also referred to as "self-introducing catheters" would be used with access ports with a port valve designed to interact with the sharpened tip without unacceptable damage and wear.

Still another aspect of this invention is a simplified means of locating the entrance orifice of an access port after implantation. Such features are provided through the use of a template which is placed over the implanted access port and provide an indication to the clinician as to the position and orientation of the inlet orifice, thus simplifying the process of locating the target area of the access port.

Additional benefits and advantages of the present invention will become apparent to those skilled in the art to which this invention relates from the subsequent description of the preferred embodiments and the appended claims, taken in conjunction with the accompanying drawings.

BRIEF DESCRIPTION OF THE DRAWINGS

FIG. 1A is a cross-sectional view of the access port assembly of FIG. 1 taken along line 1A—1A of FIG. 1.

FIG. 2 is a cross-sectional view to an access port in accordance with an embodiment of this invention in which the articulating valve comprises an elongated self-flattening elastomeric tube section.

FIG. 2A is a cross-sectional view along line 2A—2A of FIG. 2 showing the tube valve in a closed condition.

FIG. 2B is a cross-sectional view similar to FIG. 2A but showing the tube valve in an open condition.

FIG. 11 is a pictorial view of a surgical tool particularly designed for defining an incision and a subcutaneous pocket for placement of an access port such as shown in FIGS. 7 through 10.

FIG. 12 is a pictorial view of the surgical tool of FIG. 11 in an initial position shown in full lines, and a final position shown in phantom lines forming the incision and pocket for implantation of an access port.

FIG. 13 is an illustration of the implantation procedure for inserting an access port according to this invention within a subcutaneous pocket which has been previously formed.

FIG. 14 illustrates the dimensional relationship between an incision for access port placement and the lateral dimensions of the access port.

FIG. 28 is a cross-sectional view taken along lines 28—28 of FIG. 27 showing the device in a normally closed condition.

FIG. 29 is a view similar to FIG. 28 except showing the port being manually actuated to open the valve of the device.

FIG. 30 shows the access port of FIG. 26 with a external filament being fed through the device.

FIG. 31 is a cross-sectional view of a manually actuated access port in accordance with an alternate embodiment of this invention shown in a normally closed condition.

FIG. 32 is another cross-sectional view of the port of FIG. 31 except showing the port in a open condition providing access by an external filament.

FIG. 33 is another cross-sectional view of the access port of FIG. 31 after the external actuation force is relieved with the external filament in place.

FIG. 34 is a pictorial view of a manually actuated access port in accordance with an alternate embodiment of this invention having displaceable shutter type valve elements.

FIG. 35 is a cross-sectional view taken along lines 35—35 from FIG. 34 showing the device in its normally closed condition.

FIG. 36 is a cross-sectional view similar to FIG. 35 except showing the device with a manual actuation force applied and opening the valve elements.

FIG. 41 is a pictorial view of a self-introducing catheter in accordance with this invention.

FIG. 42 is an enlarged detailed view of the tip of the self-introducing catheter shown in FIG. 41.

FIG. 43 is a cross-sectional view taken along lines 43—43 of FIG. 42.

FIG. 44 is an enlarged pictorial view of the tip of an alternate embodiment of a self-inducing catheter according to this invention.

FIG. 45 is an enlarged pictorial view of another alternate embodiment of a tip for a self-introducing catheter according to this invention.

DETAILED DESCRIPTION OF THE INVENTION

Figure 1:
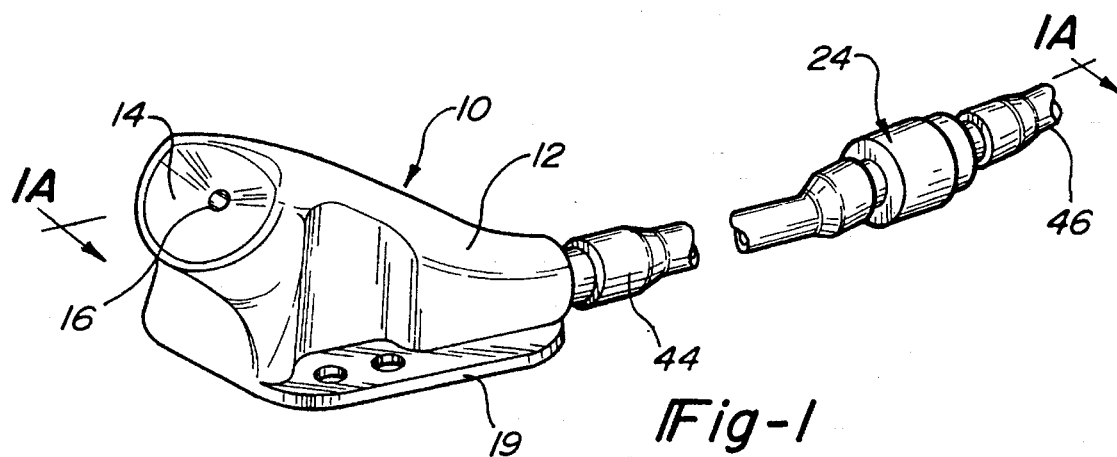
FIG. 1 is a pictorial view of an access port assembly in accordance with this invention in which the access housing and valve are separate elements connected by a flexible coupling.

With reference to FIG. 1 an access port assembly in accordance with one embodiment of this invention is shown. The major distinction of access port assembly 10 as compared with access ports described in prior related applications is the provision of a valve which is not integrated into the port housing.

Port assembly 10 includes access housing 12 which defines a funnel shaped entrance orifice 14 having a decreasing cross-sectional open area which reduces down to focus area 16 which in turn leads into passageway 18. As Shown, passageway 18 defines a bend which acts as a "needle stop", preventing a sharp rigid accessing Instrument such as a needle from passing completely through passageway 18 and out of exit nipple 20. For applications where access port assembly 10 is used with a sharp access instrument such as a needle, the inside surface 22 of entrance orifice 14 is formed of a hard material such as a metal, ceramic or other material which does not tend to be gouged by the sharp accessing instrument, but instead tends to guide it toward focus area 16.

Access housing 12 is supported subcutaneously by mounting platform 19 having holes 21 for use with sutures or staples. Valve assembly 24 which is separate from housing 12 includes two parts 26 and 28 which are threaded together. Housing part 26 includes inlet nipple 30 and housing part 28 forms outlet nipple 32. When assembled, housing parts 26 and 28 define an internal valve chamber 34 having an articulating valve. The articulating valve can take the form of any number of valve configurations as described herein, or in the related applications. Various materials can be used to produce leaflet valve elements 38 and 40. Leaflet valve elements have been made from silicone rubber sheets having a hardness valve of 27, Shore A, and a thickness of 0.040 inches. As illustrated, the articulating valve is shown in the form of a leaflet valve assembly 36 which includes a pair of leaflet valve elements 38 arid 40. Leaflet valve elements 38 and 40 and other leaflet valve elements described herein are made from a flat disk having a slit defining two or more deflectable valve leaves. In the normally closed position as shown in FIG. 1 leaflet valve assembly 36 provides resistance to the flow of the liquids across valve 24. Conduit 44 connects access housing 12 with valve 24 connecting with housing exit nipple 20 and valve inlet nipple 30. Valve outlet nipple 32 is connected to implanted catheter 46 which is tunnelled to a desired site within the patient. Alternatively, outlet nipple 32 could terminate directly at the desired patient site for example, a peripheral vein.

In use, access port assembly 10 is placed subcutaneously. If desired, access housing 12 can be fastened to support tissue using sutures or surgical staples or other mounting approaches by passing them through holes 21. It is believed unnecessary to separately mount valve assembly 24 as it is sufficiently restrained through its connection with access housing 12 and implanted catheter 46. In the event that percutaneous access is desired with implanted catheter 46, an external flexible filament 48 such as an external catheter, wire or optical fiber is fed into entrance orifice 14 and is directed into passageway 18. As mentioned previously, if a relatively rigid instrument is used to introduce the filament which may be over or inside the introducer, there may be provided a "needle stop" which prevents the introducer from passing to exit nipple 20 where it could damage conduit 44, while allowing the flexible filament to be fed through the device and engages leaflet valve assembly 36 where it causes leaflet valve elements 38 and 40 to deflect. Upon removal of external filament 46, valve 24 returns to its normal closed condition.

Now with reference to FIG. 2 an access port in accordance with another embodiment of this invention is shown which is generally designated by reference number 50. Access port 50 differs from embodiments described in this specification and in related applications in terms of the configuration of the articulating valve used. Access port 50 has an access housing identical to that shown in FIG. 1 with common elements designated by like reference numbers. In this case, the articulating valve is in the form of an elongated elastomeric self-flattened hollow tube 52 which is stretched to fit over housing exit nipple 20. Tube 52 is connected with a conventional implantable catheter or can integrally form a round cross-section catheter segment 54. FIG. 2A shows a section of tube 52 in its normal flattened condition in which the interior hollow passageway 56 thereof is occluded. Thus in a normal configuration, fluid flow is restricted from passing through tube 52. Although tube 52 would "self-open" or inflate in response to a pressure differential between interior cavity 56 and the fluid surrounding it, the characteristics of tube 52 can be controlled to provide a predetermined pressure resistance.

When access is desired via the percutaneous route, a flexible external filament is introduced into access housing 12 in any of the various manners described previously in this specification and in the related applications. Flexible filament 58 is introduced through passageway 18 and engages hollow tube 52. Continued insertion of filament 58 causes interior cavity 56 to open to permit passage of the filament. Such passage can be continued if desired until the external filament reaches the terminal end of implanted catheter 54 or beyond, or to some point past self-flattening hollow tube 52 where fluids can be withdrawn or infused as desired. Preferably, self-flattening tube 52 has an inside dimension close to the outside diameter of the external filament 58 such that a small gap or no clearance exists between them for fluid sealing. Upon withdrawal of the external filament 58, tube 52 returns to its normal self-flattened occluded condition.

Figure 3:
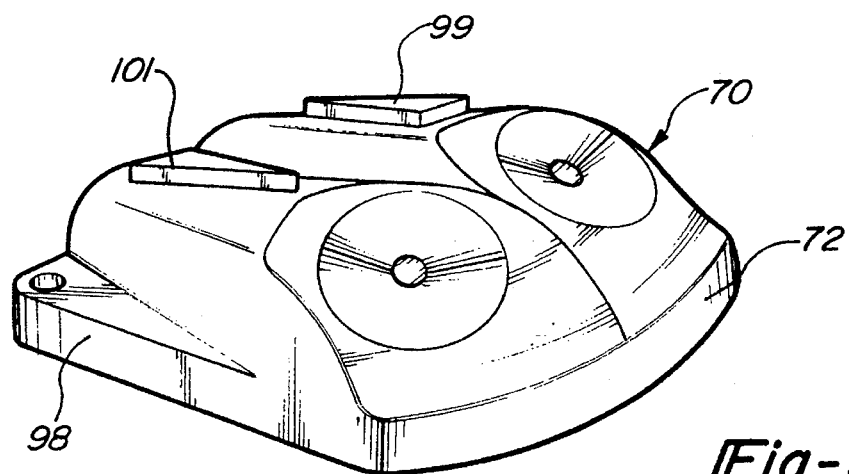
FIG. 3 is a pictorial view of an integral dual port in accordance with this invention.
Figure 4:
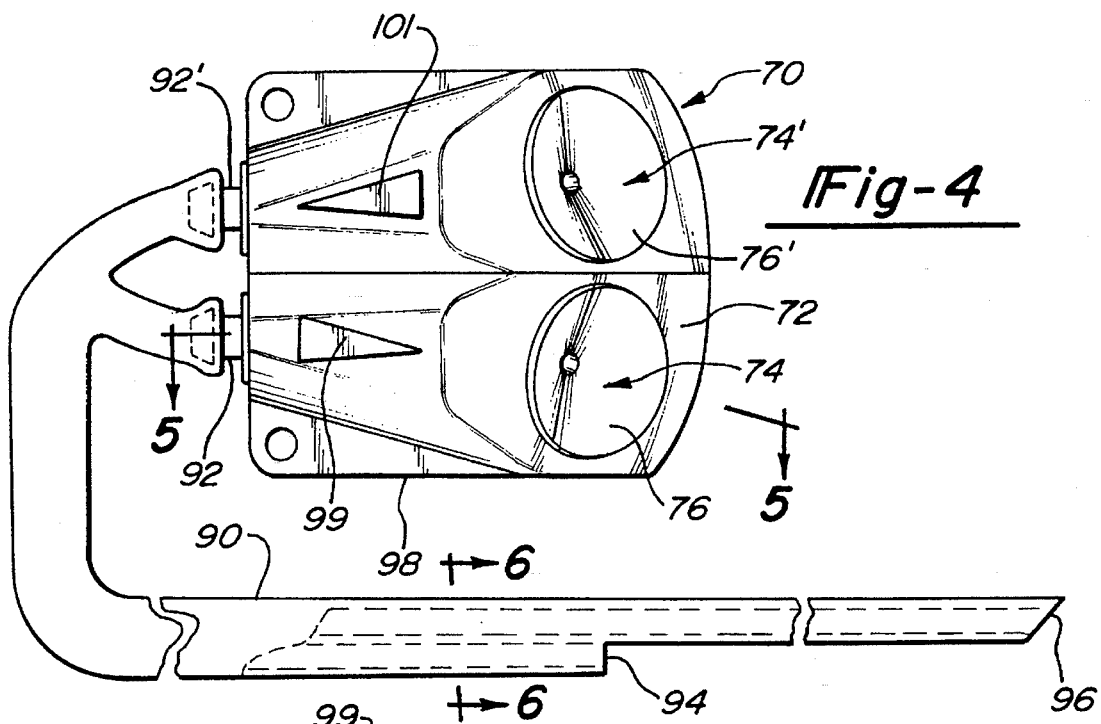
FIG. 4 is a top view of the dual access port shown in FIG. 3, shown connected to a dual lumen catheter.
Figure 5:
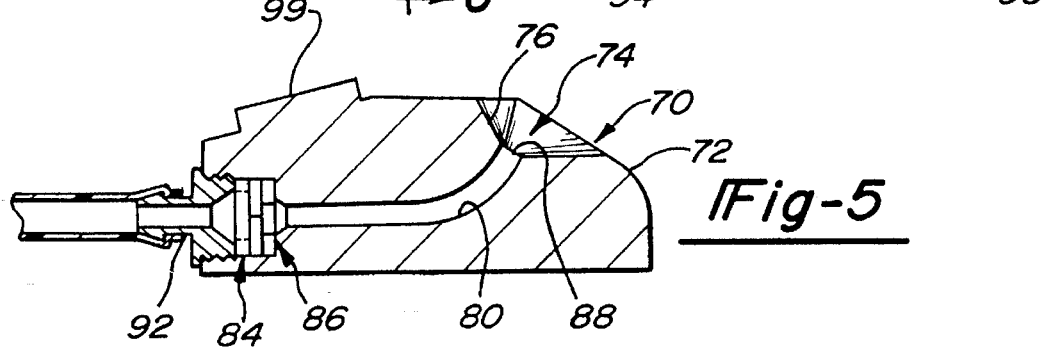
FIG. 5 is a cross-sectional view taken along line 5—5 of FIG. 4.
Figure 7:
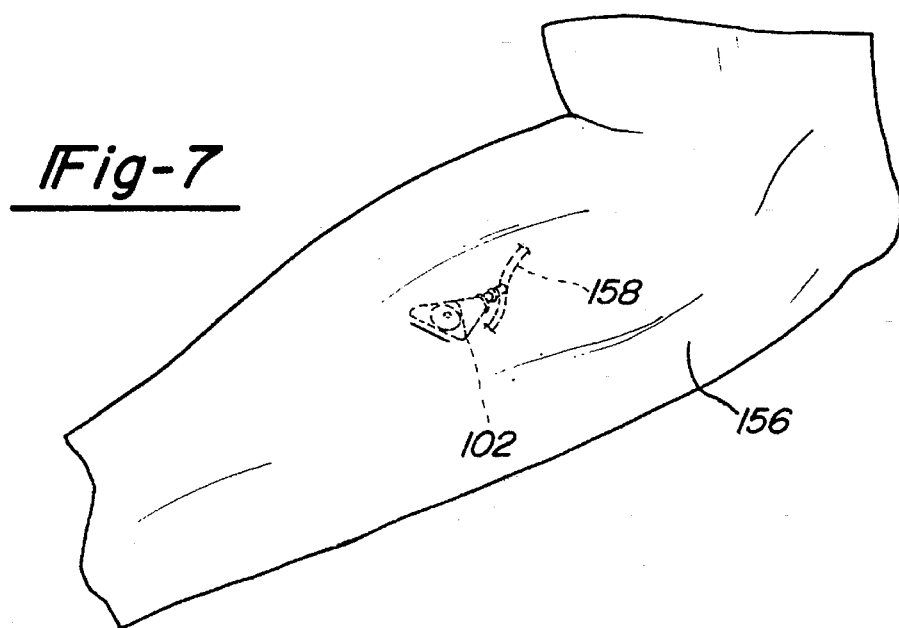
FIG. 7 is a pictorial view of the arm of a patient showing, in phantom lines, an access port implanted therein and showing an incision used for implantation.
Figure 8:
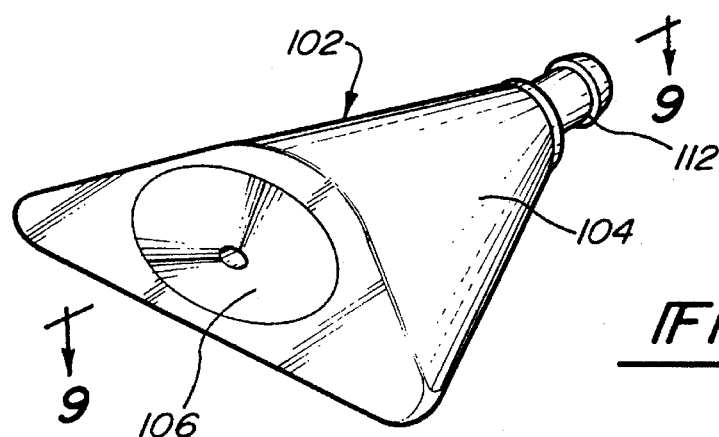
FIG. 8 is a pictorial view of the implanted access port of FIG. 7.

Now with reference to FIGS. 3 through 5 an access port in accordance with another embodiment of this invention is shown which is generally designated by reference number 70. Access port 70 differs from prior embodiments of this invention in that it incorporates the functions of a pair of separate and distinct access ports into a single device. Such device has applications where simultaneous infusion or withdrawal is needed to separate and distinct sites, or where simultaneous infusion and withdrawal of fluid is desired, for example, in hemodialysis treatment. Since ports 74 and 74' which are integrated into housing 72 are identical mirror images of one another, a description of one will suffice for both. Access port 74 has a configuration consistent with embodiments described in the related applications and includes entrance orifice 76 leading to passageway 80. Within valve chamber 84, an articulating valve is provided which in this case is a multi-element leaflet valve assembly 86. Each of the access ports 74 and 74' are accessed in a manner consistent with previously described access ports, using various types of introducing elements, and in some cases, a sharp introducer which is prevented from passing into valve chamber 84 due to the presence of a "needle stop" feature in passageway 80. In addition, the inside surface of entrance orifice 76 and portions of passageway 80 are preferably formed of a hard material for guiding a sharp pointed accessing instrument into focus area 88, and thereafter into passageway 80. Housing 72 has a mounting surface 98 for supporting the device subcutaneously.

Figure 6:
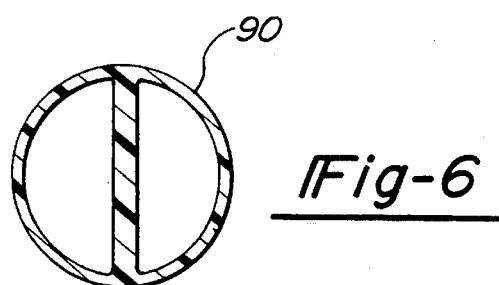
FIG. 6 is a cross-sectional view taken along lines 6—6 of FIG. 4.
Figure 37:
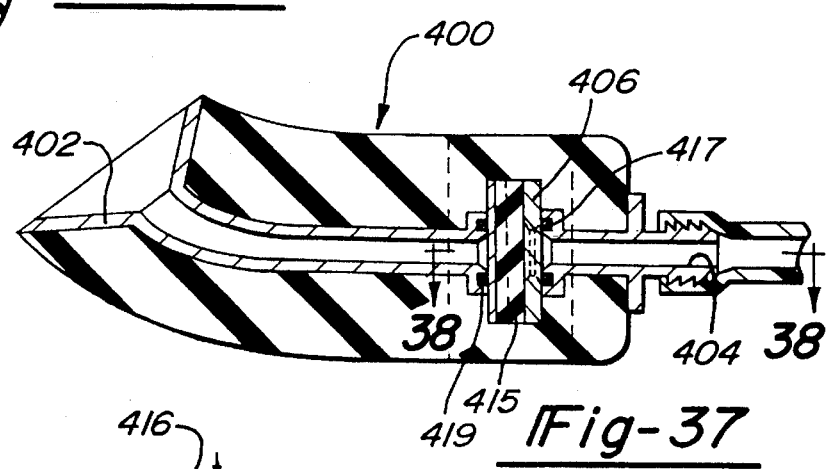
FIG. 37 is a cross-sectional view taken along line 37—37 of FIG. 35.

Access port 70 may be used with a multi-lumen implanted catheter 90 which generally defines a pair of letter "D" shaped section lumens 100 and 100', as shown in FIG. 6 which are attached at outlet nipples 92 and 92'. Multi-lumen catheter 90 includes a pair of orifices 94 and 96 which are displaced along the length of the catheter to provide separate sites for the withdrawal and infusion of fluids, such as is desired for hemodialysis treatment.

Another feature of access port 70 is the provision of external features which can be palpated after implantation which serve to differentiate ports 74 and 74'. For example, the ports may communicate with distinct sites within the body of the patient, or may be connected with lumen ports intended only for withdrawal or infusion. As shown in FIG. 3, housing 72 has a pair of arrow shaped protrusions 99 and 101 which are palpable after implantation and are oriented in opposite directions to designate intended directions of fluid flow.

Another embodiment of an access port in accordance with this invention is shown in FIGS. 7 through 10 and is generally designated there by reference number 102. Access port 102 includes housing 104 which defines a funnel shaped entrance orifice 106, which like prior embodiments, reduces down to a focus area 108 which leads to passageway 110. Exit nipple 112 is provided for attachment to an implanted catheter 114. Access port 102 differs from prior embodiments in two primary respects. First, access port housing 104 defines a generally flat supporting surface 116 which supports the port subcutaneously without the use of mounting holes for sutures or surgical staples. Second, access port housing 104 features a tapered arrow like shape, beginning with its smallest transverse cross-sectional area adjacent exit nipple 12 and enlarging when going toward entrance orifice 106. In other words, cross-sectional views taken transverse with respect to a line extending between exit nipple 112 and entrance orifice 106 have a progressively increasing cross-sectional width dimension, starting at the exit nipple and moving toward the entrance orifice. This configuration is especially adapted for simplifying the implantation procedure as will be described in more detail.

Figure 9:
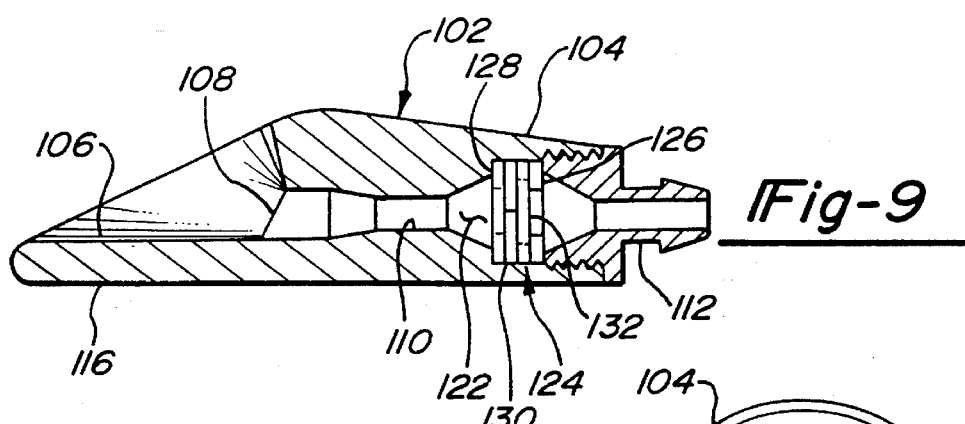
FIG. 9 is a cross-sectional view taken along lines 9—9 of FIG. 8.
Figure 10:
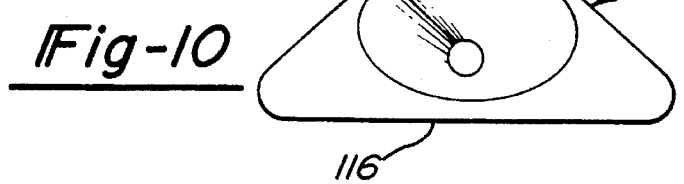
FIG. 10 is a frontal view of the port shown in FIG. 8 particular showing the entrance orifice configuration.
Figure 15:
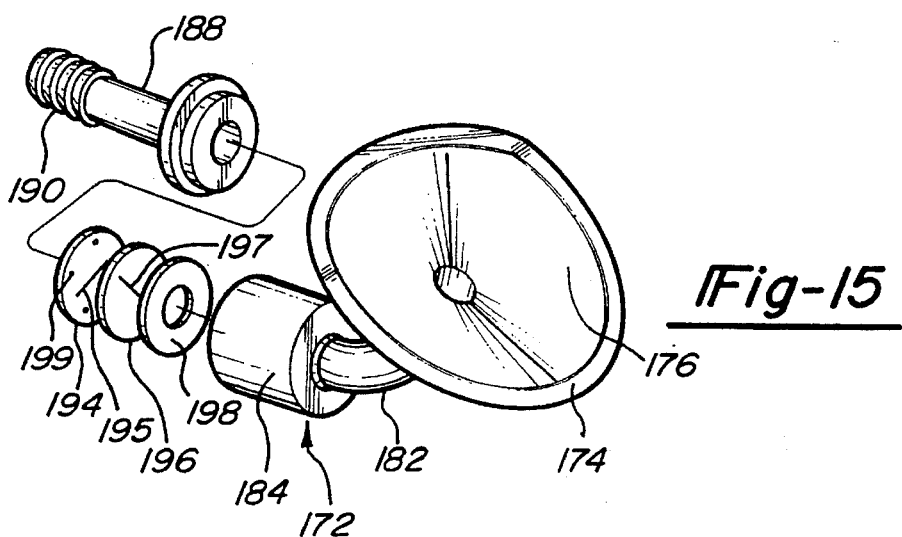
FIG. 15 is an exploded view of several components of an embodiment of a port of this invention having a composite construction.
Figure 16:
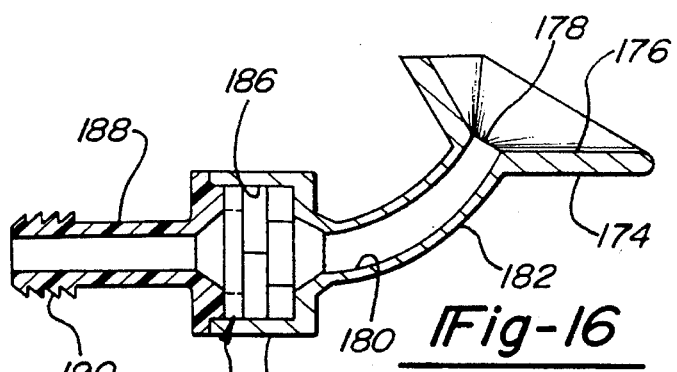
FIG. 16 is a cross-sectional view of the port components of FIG. 15.

FIG. 9 illustrates that housing 104 and exit nipple 112 define valve chamber 122. An articulating valve in the form of a multi-element leaflet valve assembly 124 is provided. Leaflet valve assembly 126 includes a pair of ring or "donut" valve elements 126 and 128, with a pair of leaflet valve elements 130 and 132 sandwich therebetween. Ring valve elements 126 and 128, and other ring valve elements described elsewhere in this specification, can be made of surgical silicone rubber having a hardness of 50, Shore A, and a thickness of 0.040 inches. As in prior embodiments, leaflet valve elements 130 and 132 are made of thin sheets of elastomeric material such as silicone rubber having one or more cuts across their surface to define two or more deflectable valve leaves. An additional description of the configuration of leaflet valve assembly 124 is provided previously in this application, and in the related applications.

Now with reference to FIGS. 11 and 12, a surgical tool especially designed to facilitate placement of access port 102 is shown which is generally designated by reference number 140. Surgical tool 140 includes a grasping handle 142 and a support disk 144. Cutting blade 146 forms a sharpened cutting tip 148 and has a right angle letter "L" configuration. FIG. 12 illustrates use of surgical tool 140 in forming an implantation pocket. The full line view of surgical tool 140 in FIG. 12 shows an initial position in which cutting tip 148 initially pierces the patient's skin 150. Surgical tool 140 is advanced to the position shown in phantom lines in FIG. 12 in which support disk 144 lies against skin 150. Cutting blade 146 is shaped to form pocket 152 which is sized for receiving and supporting access port 102.

FIG. 14 illustrates the width of incision 154 designated by "A" as related to the maximum width of port housing 104, designated by "B", and in particular, shows that dimension B exceeds dimension A. Due to the tapered configuration of access port housing 104, the access port is capable of being placed within pocket 152 through a comparatively narrow incision. As access port 102 is slid into pocket 152 through incision 154, the skin along the perimeter of the incision is stretched until the port is fully within the pocket allowing the skin to return to near its original condition. By minimizing the width of incision 154, enhanced retention and support for access port housing 104 is provided. Additional support for access port 102 is provided since pocket 152 is accurately shaped and dimensioned to receive the port.

Now with reference to FIGS. 12 and 13 a representative procedure for implantation of access port 102 within a patient's arm 156 will be described. Incision 154 and pocket 152 are formed in an appropriate manner, for example, through the use of surgical tool 140 as described previously. Skin 150 surrounding incision 154 is lifted with forceps. The position of incision 154 is intended to place port 102 near a peripheral vein 158. Vein 158 is located through pocket 152 and is penetrated using an appropriate access device. After vein 158 is penetrated, a guidewire is fed through the access device which can then be removed. Thereafter, an enlarged diameter vein dilator is placed and the guidewire is removed. Implanted catheter 114 is next fed into vein 158. In some instances it is desirable to feed the distal end of implanted catheter 114 to the patients heart or another remote site. The proximal end of implanted catheter 114 is then attached to exit nipple 112 and access port 102 is inserted into pocket 152 through incision 154. Finally, incision 154 is closed using sutures or staples.

FIGS. 15 through 18 illustrate an access port in accordance with an alternate embodiment of this invention which is generally designated by reference number 170. The primary feature of access port 170 as compared with previous embodiments is its composite construction in which certain elements are made of a hard material such as a metal or ceramic, whereas other portions are made of a non-metallic castable or moldable material such as a polymeric plastic substance. Access port 170 includes a first sub-assembly in the form of a funnel 174 which defines an inside entrance orifice 176 which reduces to a focus area 178 which in turn defines the one end of a passageway 180 formed from an elongated bent tube 182. The inside surfaces of funnel 174 and tube 182 are made of a hard material such as a metal or ceramic which is capable of guiding a sharp accessing instrument such as a hypodermic needle or trocar which enters entrance orifice 174 into focus area 178 and passageway 180.

Tube 182 can be initially straight and later bent to the configuration shown to provide a curved or smoothly bending passageway 180 which is provided to define a "needle stop" which prevents a rigid sharp accessing instrument such as a needle from passing fully through passageway 180, but permits a more flexible introduced filament such as an external catheter, guidewire or optical fiber to freely pass through passage 180 and through access port 170. It is believed that the smoothly bending passageway 180 provides advantages over the more abrupt changes in direction featured by port passageways as a "needle stops" as described In previous embodiments and in the related applications. The smoothly bending passageway 180 is believed less likely to cause kinking of the introduced flexible filament and reduces the friction imposed on the introduced filament during insertion.

Valve housing 184 joins tube 182 and defines an internal valve chamber 186. Exit plug 184 is shown press-fit into valve chamber 184 and forms exit nipple 190. Leaflet valve assembly 192 is retained in valve chamber 186 and includes a pair of leaflet valve elements 194 and 196, and ring or "donut" valve element 198; the functions of which have been fully described previously in this specification and further in the related applications. Leaflet valve elements 194 and 196 each feature single slits 185 and 187, respectively, thus defining two deflectable valve leaves per valve element. In the related applications, leaflet valve elements were shown each having three or more leaves. However, the single slit configuration of valve elements 194 and 196 has been found to provide excellent sealing capabilities, and is for many application the preferred design. Adhesive spots 99 are provided of Dow Corning Silastic Medical adhesive type A for causing the leaflet valve elements 194 and 196 to adhere to one another, enabling them to be assembled as a sub-assembly with their indexed orientation predetermined and maintained.

Figure 17:
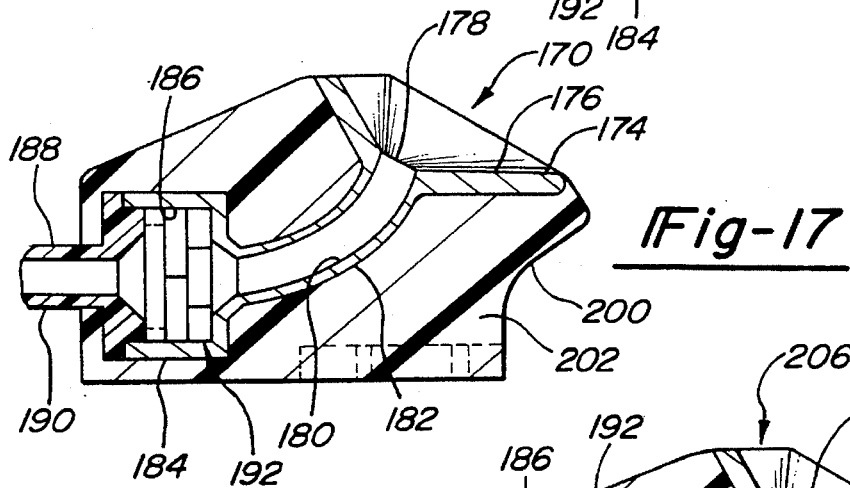
FIG. 17 is a cross-sectional view taken through a port in accordance with this invention of a composite construction.

As shown in FIG. 17 the remainder of port housing 200 is formed by a moldable or castable material 202 which encapsulates the outside surface of funnel 174, tube 182, and valve housing 184. Preferably, material 202 is formed around these components through an insert molding process in which funnel 174, tube 182, valve housing 184, and perhaps exit plug 188 are positioned within a mold cavity and thereafter the castable material 202 flows around these elements to encapsulate them. The resulting composite access port 170 can be made lighter in weight than a similar port made from an all-metal composition, increases design flexibility, and has the potential for reducing cost of manufacture.

Only those components of port 110 which need to have a hardened surface; namely, the inside surfaces of funnel 174 and passageway 180 are formed from hard material, whereas the balance of the port, including exit plug 188 can be made of castable material such as polymer plastic. In the embodiment shown, funnel 174, tube 182 and valve housing 184 are made integrally. However, in an alternate configuration, those components could be separately manufactured and later assembled.

Figure 18:
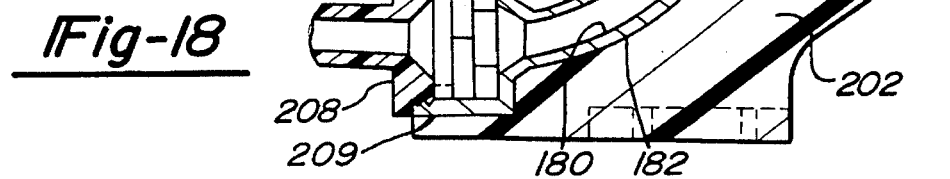
FIG. 18 is a cross-sectional view of a composite port similar to that shown in FIG. 18 except showing a modified outlet plug.

An access port 206 according to another embodiment of this invention is shown in FIG. 18 and is identical to access port 170 in many respects, and consequently common elements are identified by like reference number. The distinction of access port 206 over access port 170 relates to the attachment of exit plug 208 to valve housing 209. In the case of access port 206 this attachment is made by mating threads. In addition, exit plug 208 is not encapsulated by material 202 and remains accessible after the remainder of the unit is encapsulated. This provision enables subsequent inspection, cleaning and replacement of leaflet valve assembly 192.

Figure 19:
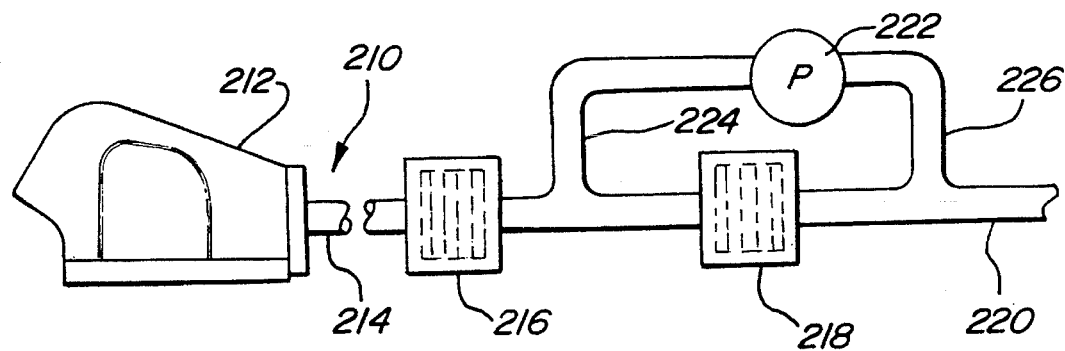
FIG. 19 is a pictorial view of an access port system in accordance with this invention used with a pair of serially connected articulating valves enabling recharging of an implanted pump also permitting access to the implanted catheter.
Figure 20:
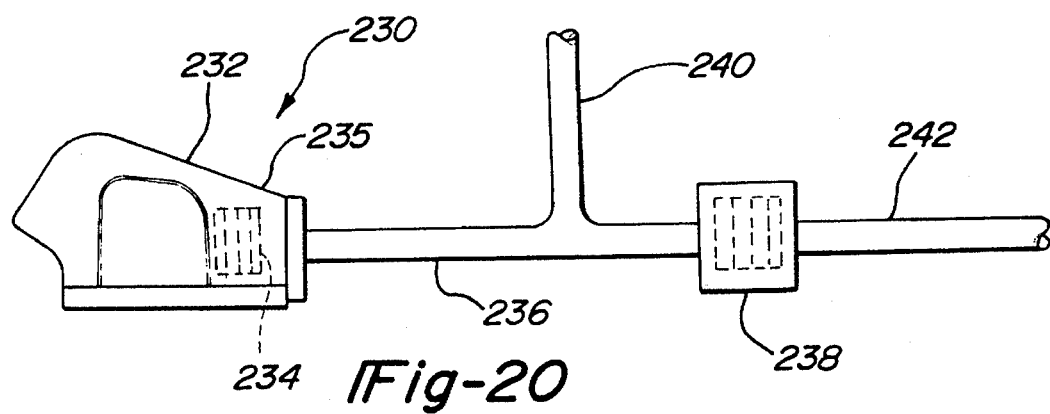
FIG. 20 shows a system similar to that of FIG. 19 providing a plural flow path.
Figure 21:
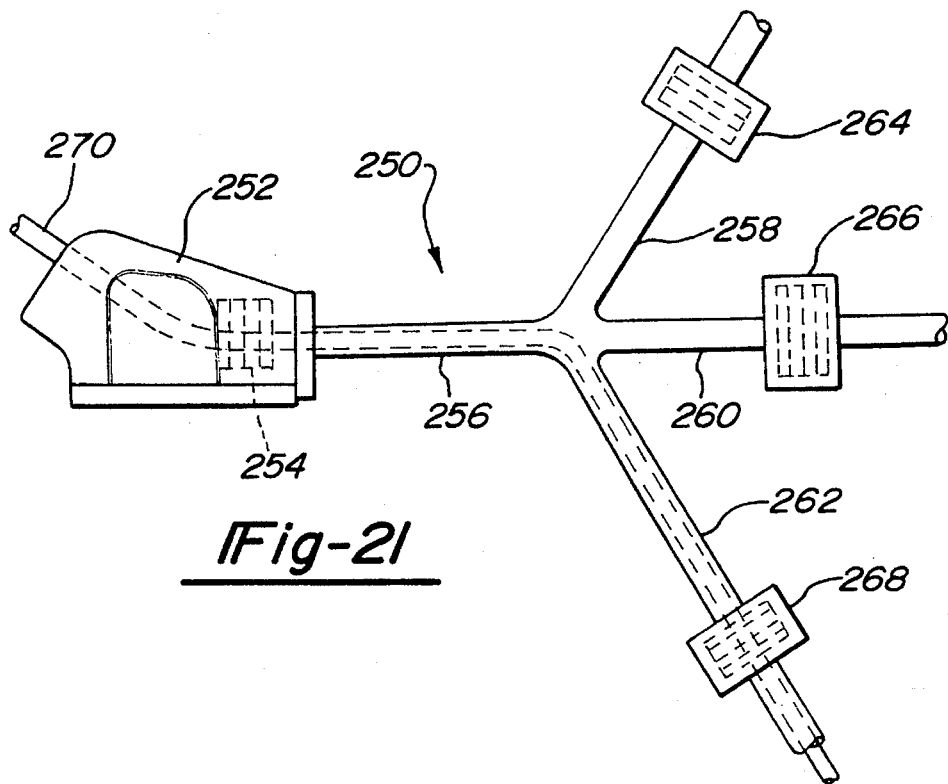
FIG. 21 is a pictorial view of an access system in accordance with this invention defining plural flow paths which are differentiated through the use of a steerable accessing filament.

Now with reference to FIGS. 19 through 21, a series of embodiments of this invention are described in which a single access port provides access to multiple sites within the body of the patient. Access system 210 shown in FIG. 19 includes an access housing 212 which is connected via implanted conduit 214 to a first articulating catheter valve 216, and thereafter, through a branching circuit 219 to a second articulating catheter valve 218, which is in turn connected via implanted catheter 220 to a predetermined site within the patient. Access housing 212 as shown is identical to access housing 12 described previously which does not incorporate an internal articulating valve, although such a configuration could be implemented, as will be apparent from the subsequent description.

Access system 210 further Includes an implanted therapy instrument shown as implantable Infusion pump 222 which Is connected to branching circuit 219 between valve assembles 216 and 218, and to branching circuit 226 which joins implanted catheter 220 at a point beyond valve 218.

Infusion pump 222 is provided for periodically administering a drug or therapeutic agent to the patient over a prolonged period. In some instances it may be desirable to replenish an internal reservoir of fluid within infusion pump 222 on a periodic basis. Currently available infusion pumps have refilling capabilities in the form of a compressed rubber septum overlying a reservoir which can be accessed using a specially designed non-coring hypodermic needle. Although such access techniques operate in a generally satisfactorily manner, they possess the disadvantage of previously available infusion ports in that they do not permit convenient and stable access to the implanted catheter such as is required for prolonged infusion or infusion of agent caustic to subcutaneous tissue.

In accordance with this invention, when it is desired to replenish infusion pump 222, an external catheter is introduced into access housing 212 and through the first articulating valve 216. Care is taken to avoid placement of the external catheter through the second articulating valve 218. A limitation in insertion length can be provided through the use of a graduated external catheter, or by choosing a catheter or accessing needle having a limited length. In this condition, fluids infused through the external catheter are directed through branch circuit 224 into infusion pump 222 where its reservoir is replenished and thereafter the external catheter is removed. Operation of implanted infusion pump 222 causes infusion to occur through branch circuit 226 into implanted catheter 220.

In the event that implanted catheter 220 needs to be cleared, repositioned, or direct access to the catheter is required, both valves 216 and 218 are penetrated by the external filament allowing the filament to be placed to the distal end of the implanted catheter and beyond. It should be noted that pump 222 could be replaced with another therapy element such as a filtration device or some type of processor. As is evident from this description, a port having an integral articulating valve can be used with the same result as a separate access housing 212 and valve 216.

Another approach toward providing a bifurcated flow system is shown in FIG. 20 in which access system 230 is shown. In this embodiment, access port 232 has a first articulating valve 234 which is formed integrated within the access port housing 235. Conduit 236 extends between access port 232 and a second articulating valve 238 and includes a branching circuit 240 which leads to a desired site within the body of the patient. The exit of the second articulating valve 238 leads to another site within the patient through implanted catheter 242.

Use of access system 230 is similar to access system 210 with the exception that partial insertion of an external filament between the two valves 234 nd 238 does not replenish an infusion pump, but instead allows infusion to one of the two remote sites within the patient. When articulating valves 234 and 238 are penetrated by the external catheter, a second remote site within the body can be accessed. Therefore, both remote sites within the patient can be accessed through implantation of a single access port 232. Access port 232 can be of a type which permits access using a needle which engages and penetrates the first articulating valve 234 as described in related U.S. Pat. No. 5,053,013. Since the access needle has a limited length, the system could be designed so that the needle would be incapable of penetrating the second valve 238. Thus assuring infusion site via branching circuit 240. If on the other hand, access to the second remote site is desired, a flexible external catheter would be introduced and sent past valve 238.

Yet another embodiment of an access system 250 providing plural pathways is shown in FIG. 21. In this embodiment, access port 252 is provided having an integral articulating valve 254. In this case, conduit 256 has a branching configuration, defining three separate branches 258, 260 and 262 each having their own in-line articulating valve 264, 266, and 268, respectively, which can be identical to articulating valve 24 as shown in FIG. 1. In this case, a selection of the flow paths defined by the branches 258, 260 and 262 is made through the use of a steerable guidewire 270 having a curved end which are in widespread use in angiography today. In some applications the first valve 254 in port 252 could be eliminated since the access housing 252 and the remote sites are isolated by the separate valves 264, 266, and 268.

Figure 22:
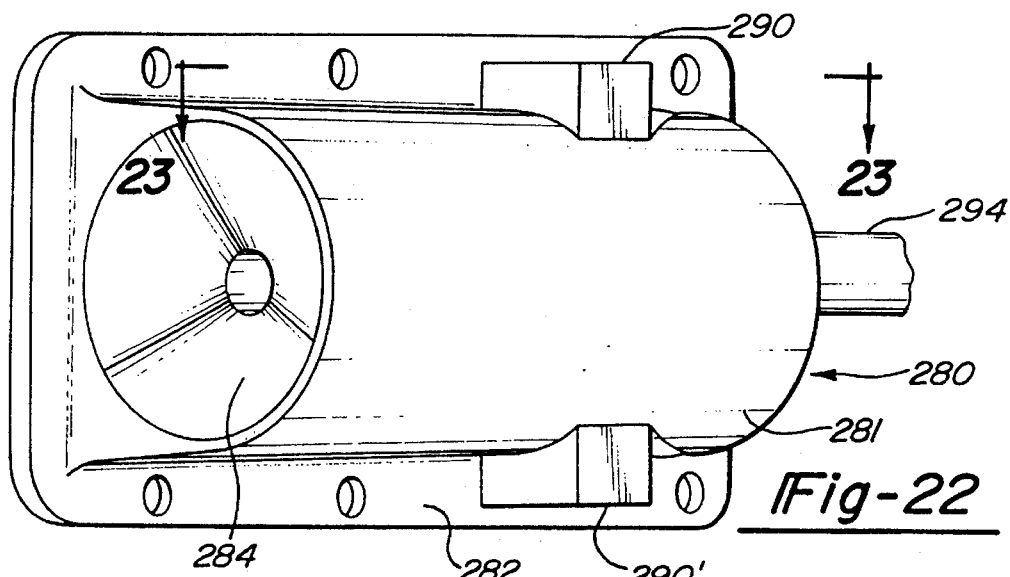
FIG. 22 is a pictorial view of a access port in accordance with an alternate embodiment of this invention having a valve which is manually actuated.
Figure 23:
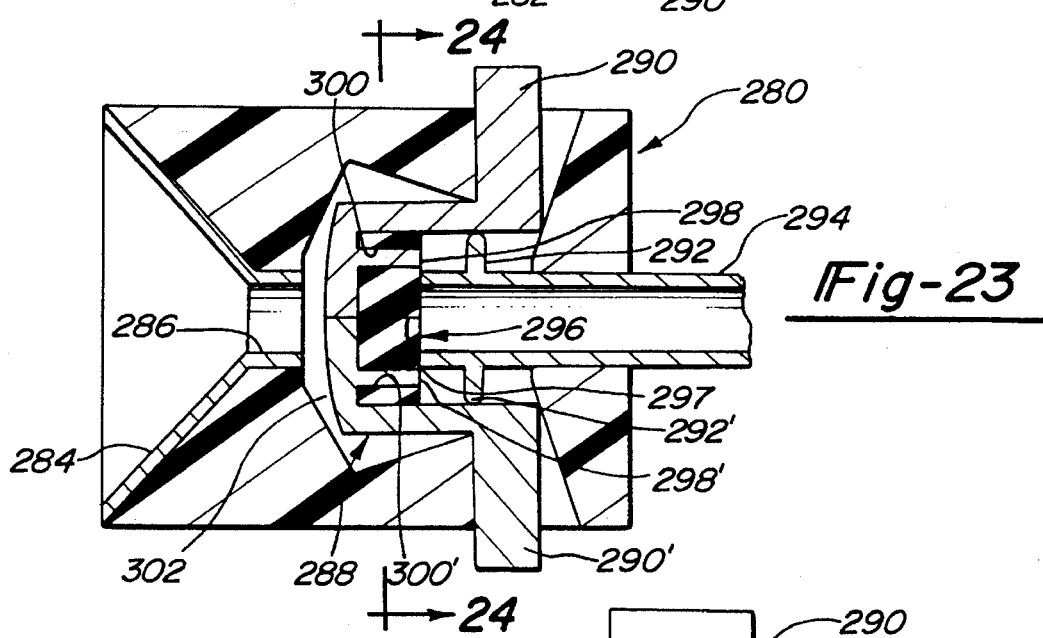
FIG. 23 is a cross-sectional view taken along lines 23—23 of FIG. 22.
Figure 24:
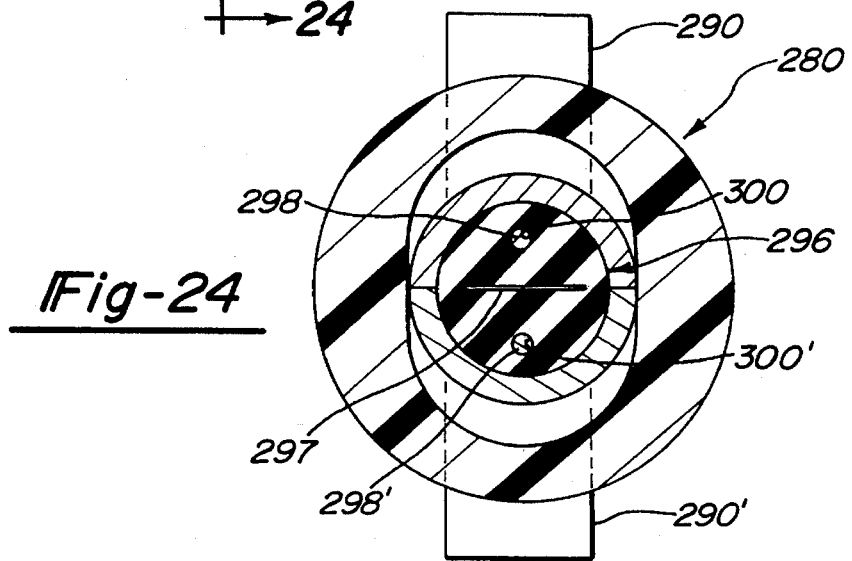
FIG. 24 is a cross-sectional view taken along lines 24—24 of FIG. 23.

Now with reference to FIGS. 22 through 36, various embodiments of access ports are described which have articulating valves which are manually actuated through external palpation by a clinician when access to the remote patient site is desired. In prior embodiments described in this specification and in the related applications, the primary mechanism for causing the articulating valve to open is through direct contact between the introduced external filament, and an element of the valve. In the following series of embodiments, external palpation of the port causes the articulating valve to be penetrated by the external filament. Access port 280 shown in FIG. 22 is one version of a manually actuated port and includes housing 281 having mounting surface 282, and as in prior embodiments, features a funnel shaped entrance orifice 284 which narrows down to passageway 286. The articulating valve assembly 288 includes a pair of actuation levers 290 and 290' which are able to pivot about fulcrums 292 and 292' formed by outlet tube 294. Elastomeric valve element 296 is retained by the actuation levers 290 and 290' through pins 298 and 298' which extend through corresponding holes 300 and 300' through the elastomeric valve element. An internal valve chamber 302 provides a clearance space for movement of actuation levers 290 and 290'. FIG. 24 shows that elastomeric valve element 296 has a slit 297 across its center, which in its normal condition acts to resist the flow of fluids through the valve.

Figure 25:
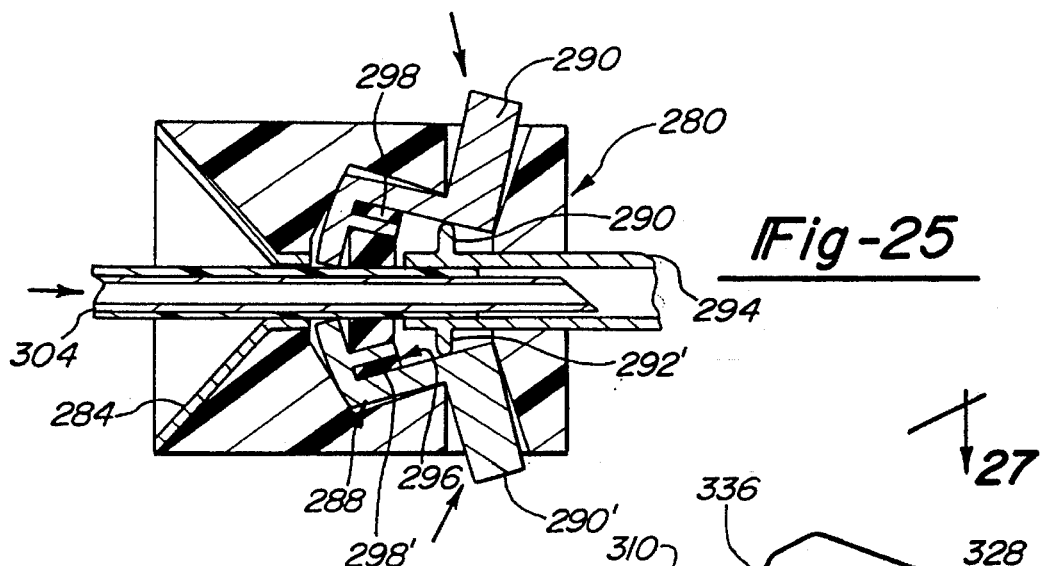
FIG. 25 is a cross-sectional view similar to FIG. 23 except showing the manually actuated valve in an open condition.

In the event that access is desired through port 280 after implantation, the clinician locates the port by palpating the skin layer overlying the port and feels the protruding actuation levers. Actuation levers 290 and 290' are then manually squeezed and urged in an inward direction. This force causes the actuation levers 290 and 290' to pivot about fulcrums 292 and 292', causing them to urge the valve element slit 297 to open as shown in FIG. 25. This opening permits an external introduced filament, in this case needle 304, to be introduced through the access port 280. When the manual force is relieved from actuation levers 290 and 290', valve element 296 tends to squeeze against needle 304 due to its elasticity which provides a desired retention force which resists a tendency for the introduced filament to inadvertently pull out of access port 280.

Figure 26:
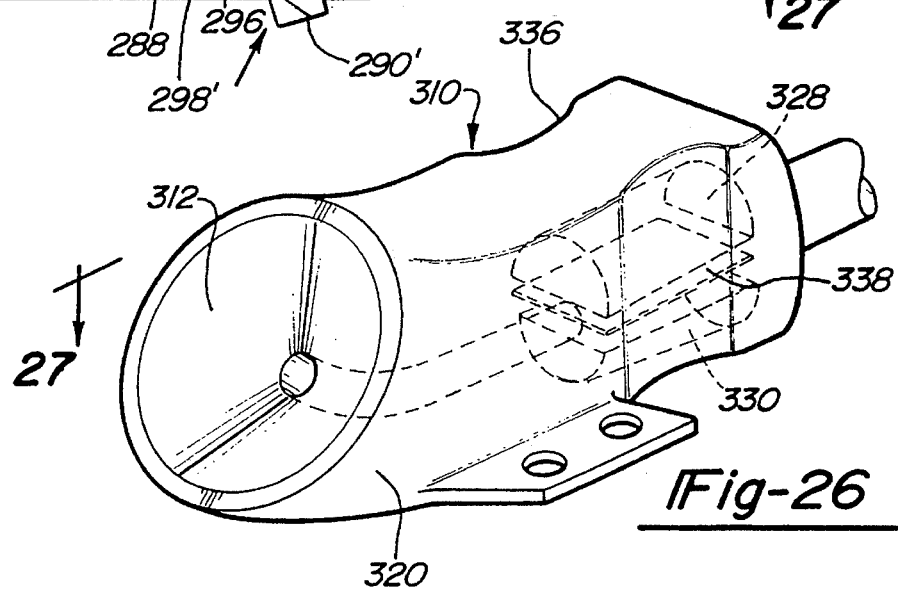
FIG. 26 is a pictorial view of a manually actuated port in accordance with an alternate embodiment of this invention showing portions of the internal features of the device in phantom lines.
Figure 27:
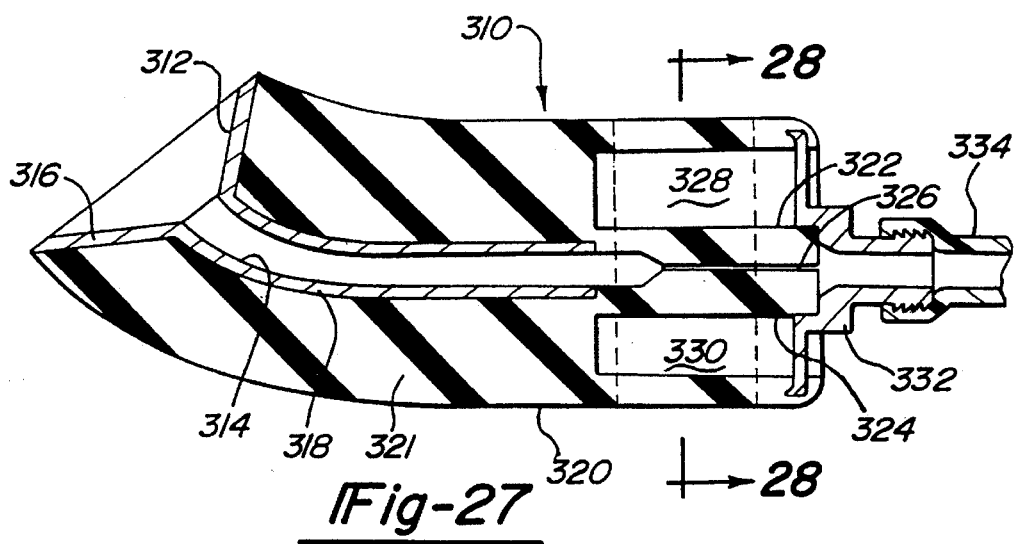
FIG. 27 is a cross-sectional view taken along lines 27—27 of FIG. 26.

Another version of a manually actuated access port is shown in FIGS. 26 through 30, and is generally designated by reference number 310. Access port 310 includes an entrance orifice 312 and passageway 314 which are formed by a metal funnel 316 and tube 318. As shown in FIG. 27, passageway 314 features a smooth bend as described previously which acts as a "needle stop". The remainder of access port housing 320 is formed by a flexible moldable material 321 such as a type of polymeric plastic material which can be insert molded around funnel 316 and tube 318, as described previously, Housing 320 defines deflectable valve elements 322 and 324 which are separated by slit 326.

As is best shown In FIG. 26, housing 320 forms a pair of semi-cylindrical cavities 328 and 330 which provide an area for the deflection of valve elements 322 and 324. Outlet plug 332 is affixed to valve elements 322 and 324 and is in turn connected to implanted catheter 334.

FIG. 28 illustrates the normal configuration of housing 320 in which valve elements 322 and 324 are normally biased to contact one another and therefore provide a fluid seal resisting the passage of fluids between entrance orifice 312 and outlet plug 332, If, however, housing indentations 336 and 338 are located and squeezed together by a clinician desiring percutaneous access, the housing is compressed laterally as shown in FIG. 29 by forces directed as indicated by the arrows in the Figure. Such forces cause housing 320 to deflect in the manner shown, causing valve elements 322 and 324 to separate such that slit 326 opens to define a passageway for external Introduced filament 340. FIG. 30 illustrates access port 310 with external filament 340 placed through the port, thus providing percutaneous access.

FIGS. 31, 32 and 33 illustrate another version of a manually actuated access port 350. In this embodiment, housing 352 defines an entrance orifice 354 which focuses down to passageway 356 and mounting platform 357. Valve chamber 358 accommodates a number of valve elements including actuator sleeve 360 which can reciprocate within the chamber and defines an internal stepped bore 362. Spring 364 urges actuator sleeve 360 toward entrance orifice 354. Insert 356 fits for reciprocation in sleeve bore 362 and defines an internal bore 368 and a cam surface 370. Seal bushing 372 is trapped within sleeve bore 362 and insert 366 as shown. Sealing ball element 374 is trapped between cam surface 370 and housing 352. Housing 352 forms an actuation post 378 whereas actuation sleeve 360 forms another actuation post 380 extending through slot 386. Implanted catheter 382 is attached to exit nipple 384 as shown.

FIG. 31 illustrates the orientation of the elements comprising access port 350 in its normal condition, i.e, when percutaneous access is not provided. Spring 364 urges actuation sleeve 360, and through compression of seal bushing 372, urges insert 366 against ball 374. The shape of cam surface 370 is such that ball 374 is jammed into sealing engagement with passageway 356 and insert bore 368, thus providing resistance to the flow of fluids through the port. FIG. 32 illustrates access port 350 being actuated to permit percutaneous access. As shown, by external palpation post 378 and 380 are pinched together causes actuation sleeve 360 to shift to the right, which in turn relieves the trapping force acting on ball 374. The external accessing instrument, in this case needle 388, is then able to urge ball 374 out of position, allowing the needle to pass through the device. FIG. 33 illustrates the accessing needle 388 passing entirely through access port 350 with the external actuation force relieved. Since ball element 374 cannot return to its normal position due to the presence of needle 388 spring 364 places a compressive force on seal bushing 372, causing its inside diameter to constrict around the outside of needle 388, thus providing a seal restricting leakage around the introduced element.

Figure 38:
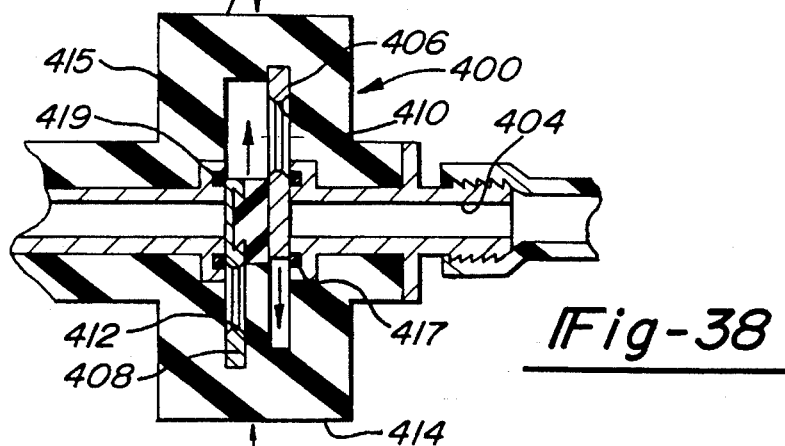
FIG. 38 is a cross-sectional view taken along line 38—38 of FIG. 37.

FIGS. 34 through 38 illustrate yet another manually actuated access port 400 in accordance with this invention. As in the prior embodiments the device incorporates a funnel shaped entrance orifice 402, passageway 404, and mounting surface 405. In this embodiment, a pair of slide elements 406 and 408 are provided, each having passages 410 and 412. Housing 412 includes a pair of projecting actuation pads 414 and 416. Housing 412 is preferably made from a flexible elastomeric material. As best shown in FIG. 38, a sealing block 415 of an elastomeric material is attached to slide element 408. A pair of "O-ring" seals 417 and 419 are positioned to confront the slide elements. Slide elements 406 and 408 are normally disposed within housing 412 such that they are displaced causing passages 410 to be disaligned, which, with the seal provided by block 415 and "O-rings" 417 and 419, providing resistance to the flow of fluid through the port. If however, actuation pads 414 and 416 are pinched together, slide elements 406 and 408 move relative to one another causing passages 410 and 412 to become aligned as shown in FIG. 36 which are also in alignment with passageway 404. In this condition, an introduced external filament can be fed entirely through access port 400. By relieving the pressure on actuation pads 414 and 416, slide elements 406 and 408 are urged to return to their normal condition shown in FIG. 35 which places a shear force on the external filament. The shear force is maintained at a level that will not damage the external filament but provides a desired friction against inadvertent withdrawal of the filament from the port.

Figure 39:
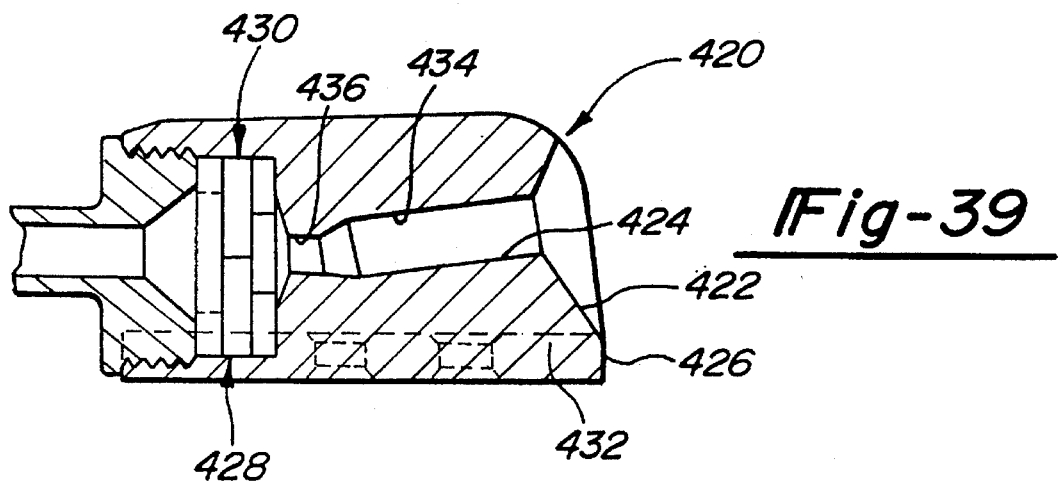
FIG. 39 is a cross-sectional view of a access port in accordance with an alternate embodiment of this invention having an inlet passageway with a restricted diameter providing a needle stop.
Figure 40:
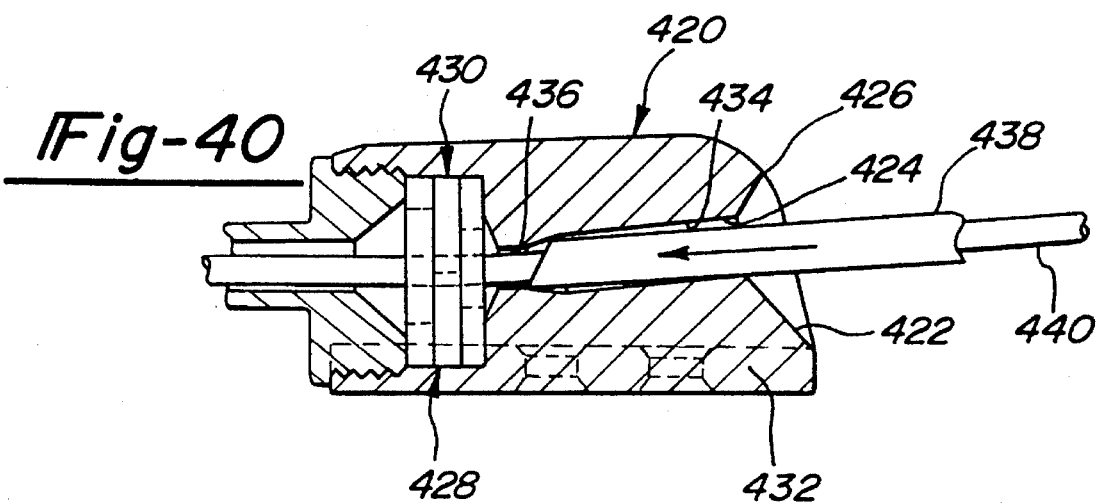
FIG. 40 shows the access port of FIG. 39 with an access needle engaging the reduced diameter region of the housing passageway.

FIGS. 39 and 40 illustrate access port 420 in accordance with an alternate embodiment of this invention, which, like the prior embodiment, features housing 426 with funnel shaped entrance orifice 422 leading to passageway 424. Housing 426 defines valve chamber 428 including an articulating valve in the form of a leaflet valve assembly 430. Housing 426 further forms a mounting platform 432. Access port 420 differs from prior embodiments with respect to the form of "needle stop" used to prevent a sharp access instrument such as a needle or trocar from engaging and possible damaging leaflet valve assembly 430. In prior embodiments the entrance passageway underwent a change in direction to prevent the rigid Instrument from engaging the valve assembly. In this embodiment, however, passageway 424 features a stepped inside diameter, beginning with enlarged diameter section 434 and reducing to smaller diameter section 436. Access port 420 is designed to be used in a system in which a large caliper needle 438 is used for accessing, with the introduced flexible filament 440 introduced through its center.

FIG. 40 shows the accessing procedure for port 420 in which the needle 438 is prevented from passing into smaller diameter section 436 due to its diameter. The flexible filament 440, however, is permitted to freely engage and pass through leaflet valve assembly 430.

FIGS. 41 through 45 illustrate various embodiments of flexible accessing filaments which include sharpened points so that they can be "self-introduced". In other words, these external filaments can be introduced through the skin and underlying subcutaneous tissue into an access port in accordance with this invention without requiring a separate sharp accessing instrument such as a needle or trocar (to puncture the skin and subcutaneous tissue) with the introduced filament placed around or inside the introducer. Self introducing catheter 450 as shown in FIG. 41, features connector 452, hollow filament 456, and pointed metal tip 454. Pointed tip 454 is bonded or otherwise attached to hollow filament 456 which can be made from various bio-compatible material such as Nylon or other materials presently used for making catheters. As shown in FIG. 42, pointed tip 454 includes a circular port 458 enabling fluid communication between the Inside lumen of filament 456 and the site to which access is desired. FIG. 43 illustrates the means of interfitting pointed tip 454 with filament 456.

FIG. 44 illustrates an alternate embodiment of the self-introducing catheter 462 which differs from the prior embodiment in that the fluid communication port 464 is provided within filament 466. In FIG. 43, another alternate embodiment of a self-introducing catheter 468 is shown in which pointed tip 470 has a triangular shaped orifice 472.

In use, self-introducing catheters 450, 462 and 468 are positioned with the pointed tip in the area of the implanted port entrance orifice. The self-introducing catheter is pushed, forcing the pointed tip through the skin where it engages the port entrance orifice where it is directed through the port. The configuration of pointed tip 454 with its conical shape is believed to be less traumatic to the patient as compared with conventional hypodermic needle having a bevel end cut. In addition, the positioning of the pointed tip at the center of the catheter is believed to be less likely to damage the soft components of a leaflet valve assembly, thus providing repeated access capability.

Figure 46:
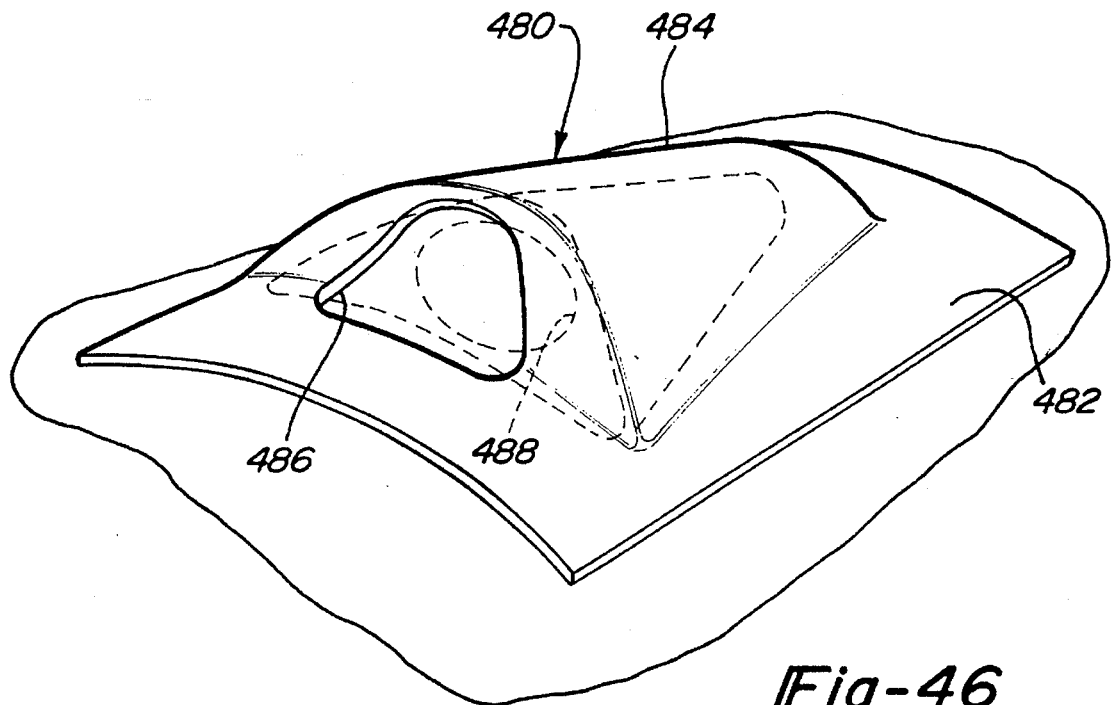
FIG. 46 is a pictorial view of a template for facilitating location of an implanted access port entrance orifice.
Figure 47:
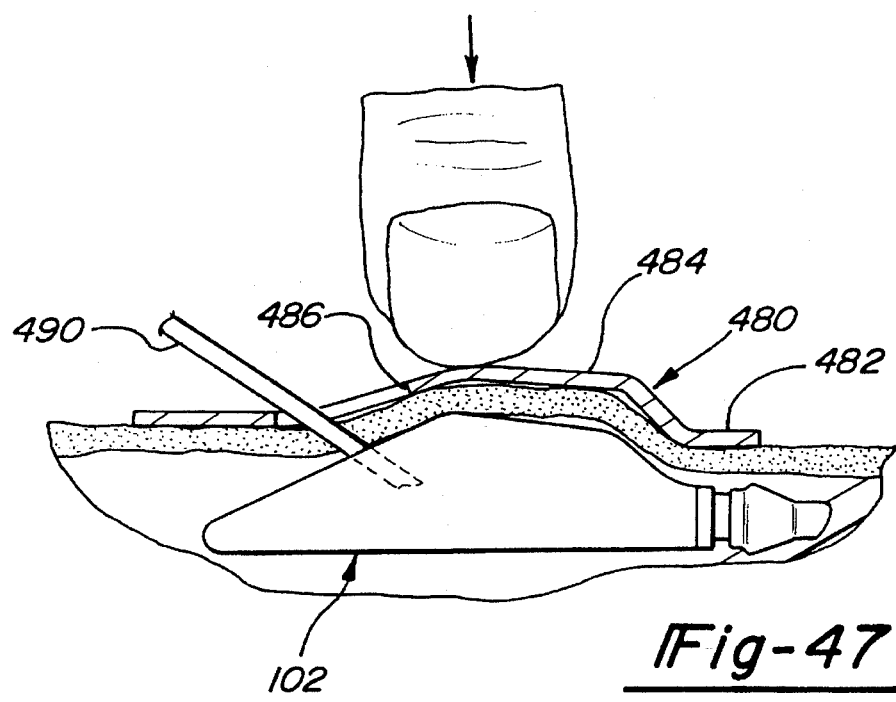
FIG. 47 is a cross-sectional view of the template of FIG. 46 shown being used to access an implanted access port.

FIGS. 46 and 47 illustrate a template 480 which enables convenient access to a previously implanted access port in accordance with this invention. Template 480 includes a base surface 482 which fits on the patient's skin having a hump 484 which is shaped to conform to the patient's skin after an access port has been implanted. Template 480 has aperture 486 which defines a target area which aids in orienting the accessing instrument into an area which overlies port entrance orifice 488 which underlies the skin as shown in phantom lines in the figure. FIG. 47 shows accessing needle 490 penetrating the skin as the template 480 is held in position.

While the above description constitutes the preferred embodiments of the present invention, it will be appreciated that the invention is susceptible of modification, variation and change without departing from the proper scope and fair meaning of the accompanying claims.

I claim:

1. A method of providing repeated access to a preselected site within a patient by an external filament comprising the steps of:

providing an access port having a housing including an entrance orifice, an exit orifice and a passageway connecting the entrance orifice to the exit orifice, providing a catheter, making an incision in the patient's skin, locating the site within the patient through the incision, affixing one end of the catheter to the site, affixing an opposite end of said catheter to the access port exit orifice, inserting the access port through the incision to a subcutaneous position, and closing the incision.

2. A method according to claim 1 wherein the access port includes means for enabling the incision to be stretched open during said insertion step, said incision being made to a dimension which results in the stretching of the incision when the port is inserted thereinto.

3. A method according to claim 2 wherein the site is a peripheral vein in the arm of the patient.

4. A method according to claim 2 further comprising the steps of providing a cutting tool having a blade for forming said incision and cutting a subcutaneous pocket for receiving said port and using said tool to form said incision and said pocket.

5. A method of providing repeated access to a peripheral vein within a patient by an external filament such as an external catheter, needle, wire or optical fiber, comprising the steps of:

providing an access port having a housing forming an entrance orifice for receiving said filament and an exit orifice, said access port having a shape in which its cross-sectional dimension enlarges from said exit orifice to said entrance orifice, providing a catheter, making an incision in the patient's skin, locating the vein through the incision, affixing one end of the catheter to the vein, affixing an opposite end of the catheter to the port exit orifice, inserting the port through the incision to a subcutaneous position, and closing the incision.

6. An implantable patient access port according to claim 1 wherein the port increases in width along smooth surfaces from the exit orifice toward the entrance orifice until reaching a maximum width, the port also increases in height along smooth surfaces from the exit orifice toward the entrance orifice until reaching a maximum height.

7. An implantable patient access port according to claim 1 wherein said step of making the incision includes the step of making the incision to a width which is less than the maximum width of the port.

8. An implantable patient access port according to claim 7 wherein said step of inserting the port through the incision includes the step of stretching the skin defining the incision to form a layer opening.

9. An implantable patient access port according to claim 8 wherein said stretching step includes the step of using the port to stretch the skin defining the incision.

* * * * *